US007297298B2

(12) United States Patent
Matsunami et al.

(10) Patent No.: US 7,297,298 B2
(45) Date of Patent: Nov. 20, 2007

(54) NANO-PARTICLES AND PROCESS FOR PRODUCING NANO-PARTICLES

(75) Inventors: Yuki Matsunami, Shizuoka (JP); Shintaro Washizu, Shizuoka (JP)

(73) Assignee: Fujifilm Corporation, Tokyo (JP)

( * ) Notice: Subject to any disclaimer, the term of this patent is extended or adjusted under 35 U.S.C. 154(b) by 550 days.

(21) Appl. No.: 10/738,092

(22) Filed: Dec. 18, 2003

(65) Prior Publication Data

US 2004/0166166 A1  Aug. 26, 2004

(30) Foreign Application Priority Data

| Dec. 25, 2002 | (JP) | ............................. 2002-374381 |
| Aug. 21, 2003 | (JP) | ............................. 2003-298035 |
| Nov. 18, 2003 | (JP) | ............................. 2003-387968 |
| Nov. 18, 2003 | (JP) | ............................. 2003-387971 |

(51) Int. Cl.
    *B29B 9/00*   (2006.01)
(52) U.S. Cl. .......................................................... 264/5
(58) Field of Classification Search ..................... None
    See application file for complete search history.

(56) References Cited

U.S. PATENT DOCUMENTS

2002/0068795 A1* 6/2002 Won et al. .................. 525/100

FOREIGN PATENT DOCUMENTS

| JP | 2002-179820 A | 6/2002 |
| JP | 2006-225668 A | 8/2006 |
| JP | 2006-225669 A | 8/2006 |
| JP | 2006-273936 A | 10/2006 |
| WO | WO 98/30604 A1 | 7/1998 |

OTHER PUBLICATIONS

Hong Xie et al., "Dendrimer-mediated synthesis of platinum nanoparticles: new insights from dialysis and atomic force microscopy measurements", Nanotechnology 16 (2005) S492-S501.

* cited by examiner

*Primary Examiner*—Mary Lynn Theisen
(74) *Attorney, Agent, or Firm*—Sughrue Mion Pllc.

(57) ABSTRACT

It is an object of the present invention to provide a process for producing nano-particles, capable of efficiently producing monodisperse nano-particles substantially uniform in particle size and composition, and freely controllable in particle size and composition at low cost. The process for producing nano-particles comprises a particle precursor capturing step in which a liquid containing the particle precursor is incorporated in another liquid containing dendritic branching molecules to capture the particle precursor by the dendritic branching molecule, and particle forming step in which the particle precursor captured by the dendritic branching molecule is transformed into the particle.

21 Claims, 6 Drawing Sheets

NANO-PARTICLES AND PROCESS FOR PRODUCING NANO-PARTICLES

BACKGROUND OF THE INVENTION

1. Field of the Invention

The present invention relates to a process for producing nano-particles, capable of efficiently producing monodisperse nano-particles substantially uniform in particle size and composition and freely controlling the particle size and composition, and also to nano-particles.

2. Description of the Related Art

Nano-particles, which may be of inorganic or organic compound or the like, mean particles of 500 nm or less in size, and are expected to go into various areas, e.g., cosmetics, perfumes/deodorizers, seasonings, ink jet materials, recording materials and catalysts. For example, they are expected to be applicable to highly active catalysts which can achieve a specific object in a small quantity, with their large specific area. They are also expected to exhibit functions different from those provided by the bulk materials, e.g., quantum effect, by utilizing their long light wavelengths, or their size smaller than mean free paths of electric conductors or than magnet domains.

For nano-particles to exhibit their functions, it is essential to control their size and composition. In particular, it is essential to sharply control their size and composition for them to exhibit the quantum effect. Moreover, processes for stably producing nano-particles are needed for their commercialization. However, there are many problems to be solved before they are commercialized, e.g., those involved in stabilization, dispersion, film-making, bulk material production and handling. Still more, processes for stably producing nano-particles with well-controlled morphology and interfaces are needed.

Processes for producing the nano-particles include evaporation/flocculation, vapor-phase processes, including vapor-phase reaction processes, chemical precipitation and liquid-phase processes, including solvent evaporation. Refer to Masaaki Koyama, New Ceramics, vol. 8, p. 79, 1990, Nobuyuki Kikugawa, Ceramics, vol. 34, p. 110, 1999, Hisao Suzuki, Ceramics, vol. 34, p. 76, 1999, and Advanced Technology for Nano-materials, edited by Mitsue Koizumi et al, CMC, for details.

However, none of the above nano-particle production processes can sufficiently control sharp particle size and composition. Moreover, it is difficult for these processes to freely control particle composition. For example, even for the nano-particles expected to exhibit a catalytic function, which depends only on the surface composition, the whole particle and surface are required to have the same composition.

On the other hand, a tree-shape, branched polymer has a completely uniform metal coordination number between the molecules. Therefore, it is expected that a sharp particle size and composition can be controlled, if a metal coordinated in each tree-shaped, branched polymer molecule is solidified to prepare a nano-particle. Nano-size metallic clusters which include a tree-shape, branched polymer having metal coordination capacity inside are disclosed by, e.g., Japanese Patent Application Laid-open (JP-A) No. 2001-508484, D. A. Tomalia et al, J. Am. Chem., Soc., vol. 120, p. 7355, 1998, and R. M. Crooks et al, ACC. Chem. Res., vol. 34, p. 181, 2001.

However, the process for preparing particles which include a tree-shape, branched polymer involves a practically serious problem, because the particle cannot be prepared in a controlled manner, when number of the metallic atoms it contains exceeds metal coordination number. In other words, it is difficult to obtain the particle having a size of 5.0 nm or more and containing 5000 or more metal atoms, knowing that a tree-shape, branched polymer has a metal coordination number of substantially below 5000.

Therefore, it is necessary to increase generation number of a tree-shape, branched polymer, in order to increase metal coordination number of the polymer and thereby increase size of the particle. Increasing its generation number, however, needs more reaction steps, which should greatly complicate the synthesis process. Moreover, increasing its generation number increases density of the atoms on the polymer surface, and is limited from the molecular structure. Still more, it is difficult to improve stability and functionality of the particle by forming therein a core-shell structure exhibiting a function of securing a composition on the particle surface different from that inside.

Objects and Advantages

It is an object of the present invention to provide a process for producing nano-particles, capable of efficiently producing monodisperse nano-particles substantially uniform in particle size and composition. It is another object of the present invention to provide nano-particles produced by the same process.

SUMMARY OF THE INVENTION

The process of the present invention for producing nano-particles comprises 2 steps, one incorporating a liquid containing a particle precursor in another liquid containing dendritic branching molecules to capture the precursor by the dendritic branching molecule (particle precursor capturing step), and the other transforming the precursor captured by the dendritic branching molecule into the particle (particle forming step).

In the particle precursor capturing step, a liquid containing the particle precursor is incorporated in another liquid containing the dendritic branching molecules to capture the precursor by the dendritic branching molecule. In the particle forming step, the precursor captured by the dendritic branching molecule is transformed into the particle. The dendritic branching molecule has substantially uniform focal sites (sometimes referred to as focal points). Therefore, the process of the present invention can produce the substantially monodisperse particles, because the individual metallic ion captured by the substantially uniform focal site is selectively allowed to participate in the reaction. The individual metal ion in the metal ion solution is reacted with at least one of a reducing reagent and specific reagent, after being captured by the dendritic branching molecule, to form the nano-particle.

As a result, the process of the present invention for producing nano-particles can efficiently produce monodisperse nano-particles whose size and composition can be freely controlled.

The nano-particles of the present invention are monodisperse ones whose size and composition can be freely controlled, because they are produced by the process of the present invention for producing nano-particles. As such, they are applicable to all areas which use nano-particles of metal, semiconducting crystal, metallic chalcogenide or metal halide.

DESCRIPTION OF THE PREFERRED EMBODIMENTS

Process for Producing Nano-particles

Figure 1:
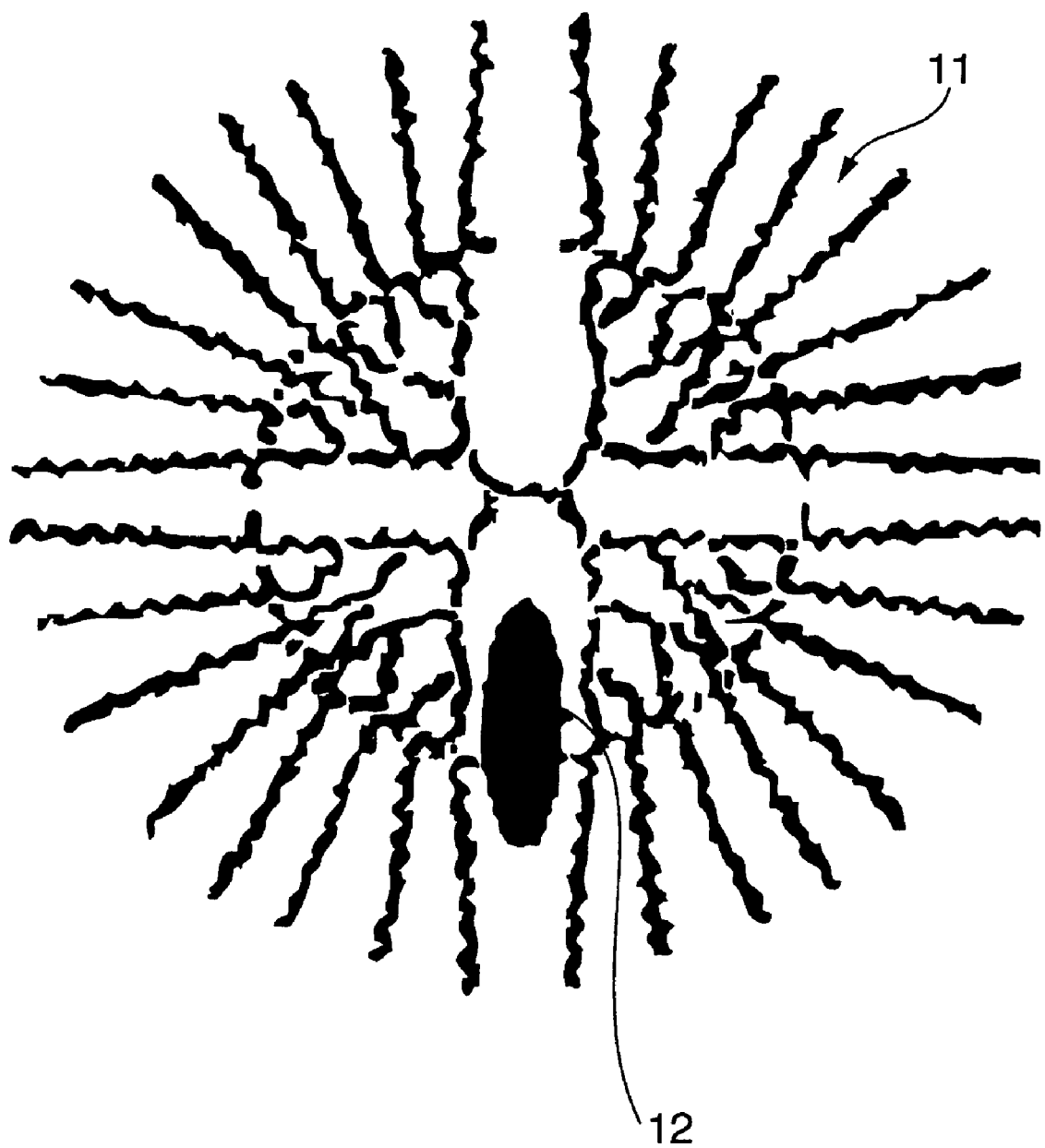
FIG. 1 illustrates one example of a particle of three-dimensional, dendritic branching polymer and inorganic particle.

The process of the present invention for producing nano-particles comprises a particle precursor capturing step and a particle forming step, and may further comprise a particle growing step. Moreover, it may further comprise one or more steps, as required.

<Particle Precursor Capturing Step>

The particle precursor capturing step incorporates a liquid containing a particle precursor in another liquid containing dendritic branching molecules to capture the precursor by the dendritic branching molecule.

Dendritic Branching Molecules

The dendritic branching molecules are those having a specific number of focal sites (sometimes referred to as focal points), and are preferably monodisperse, dendritic branching molecules. These molecules include not only a dendrimer consecutively branching regularly from a core as a branching center, but also a fan-shape, dendritic branching molecule (e.g., dendron) consecutively branching regularly from the core except for a substitute left in the molecule, which has no branch at the focal site, and hyper-branch polymer of lower regularity.

The dendritic branching molecule may be contained in part of another material. More specifically, it may be bound to another polymer or material at its functional group on the surface, or an organic compound containing a dendritic branching molecule. For example, a molecule whose dendrimer is bound to a main polymer chain at the surface, and molecule whose fan-shape, dendritic branching molecule is bound to a main polymer chain at the branching center are also within the category of the dendritic branching molecule of the present invention.

The dendritic branching molecule is not limited, so long as it has a dendritic (tree-shape), branched structure, and may be selected for a specific purpose. For example, these molecules include a dendritic (tree-shape), branched one, and fan-shape, tree-shape, branched one.

Preferable examples of the tree-shape, branched polymers include a hyper-branch polymer, and endrimer consecutively branching regularly from a core as a branching center.

Preferable examples of the fan-shape, tree-shape, branched polymers include a dendron.

The dendritic branching molecule (in particular dendrimer) preferably has a weight-average molecular weight of 200 or more, more preferably 1,500 to 100,000. A dendritic branching molecule having a weight-average molecular weight of below 200 may not have nano-particles formed therein.

The dendritic branching molecule (in particular dendrimer) preferably has a generation number of 1 or more, more preferably 2 to 10. A dendritic branching molecule having a generation number of below 1 may not have nano-particles formed therein.

Generation number of the dendron is not limited, but preferably 1 top 10.

Examples of dendrimers are given by G. R. Newkome, C. N. Moorefield and F. Figtree: "Dendrimers and Dendrons" (2001, published by WILEY-VCH); C. J. Hawker et al: J. Chem. Soc., Commun., p. 1010 (1990); D. A. Tomalia et al: Angew. Chem. Int. Ed. Engl., Vol. 29, p. 138 (1990); C. J. Hawker et al: J. Am. Chem. Soc., Vol. 112, p. 7638 (1990), and J. M. J. Frechet: Science, Vol. 263, p. 1710 (1994).

The preferable dendritic branching molecules include the molecules (1) to (14), described below.

Of these, dendrimers of the molecules (1) to (8) are more preferable, when nano-particles of core-shell structure exhibiting a function on the particle surface different from that inside.

When composite nano-particles covering a monodisperse particle having a small, uniform size are to be produced, on the other hand, a dendron having mercapto group on a focal site is more preferable. These dendrons are of the molecules (9) to (11). In this case, the particle precursor is captured by mercapto group at 2 or more focal sites. The resulting composite nano-particle is of reversed micelle structure and has improved dispersibility in a resin or the like. These particles are easily configured, because of their self-collecting characteristics, and have a sharp size distribution.

<Dendritic Branching Molecule (1): Amide Type Dendrimer>
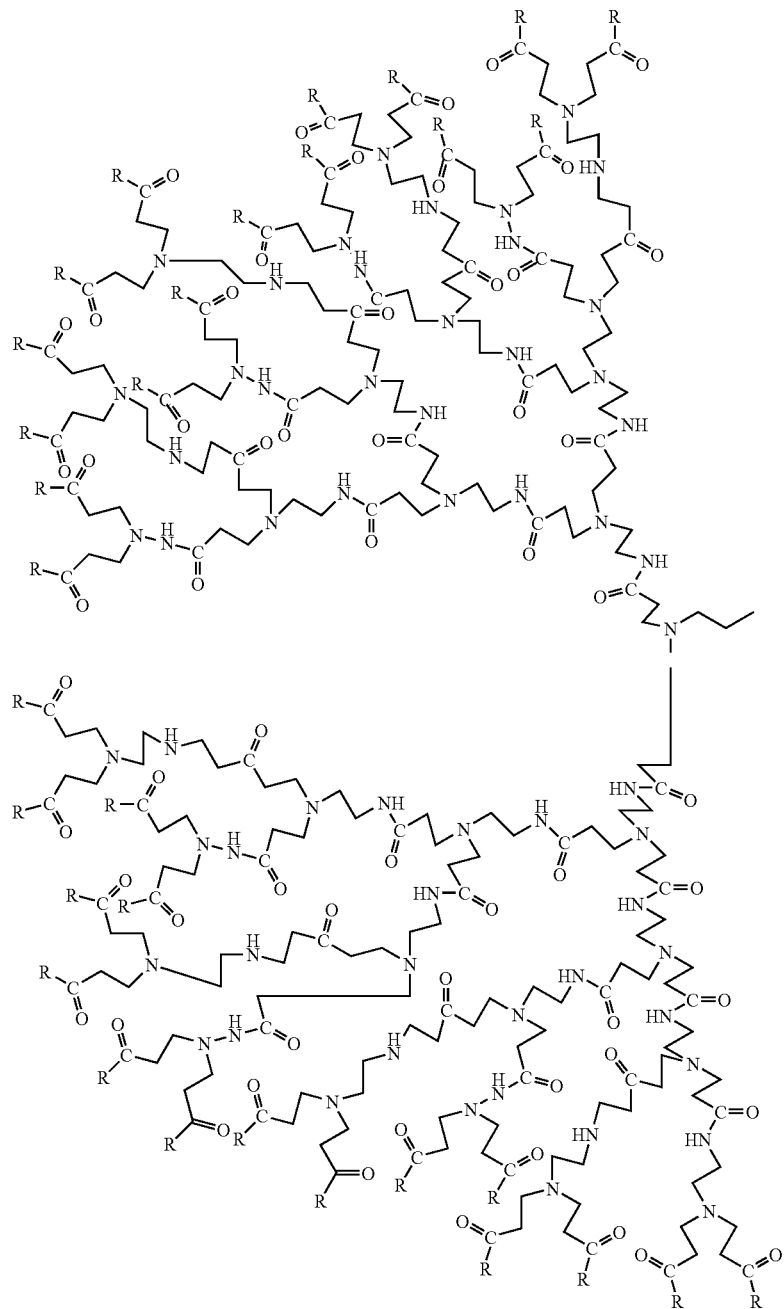

-continued
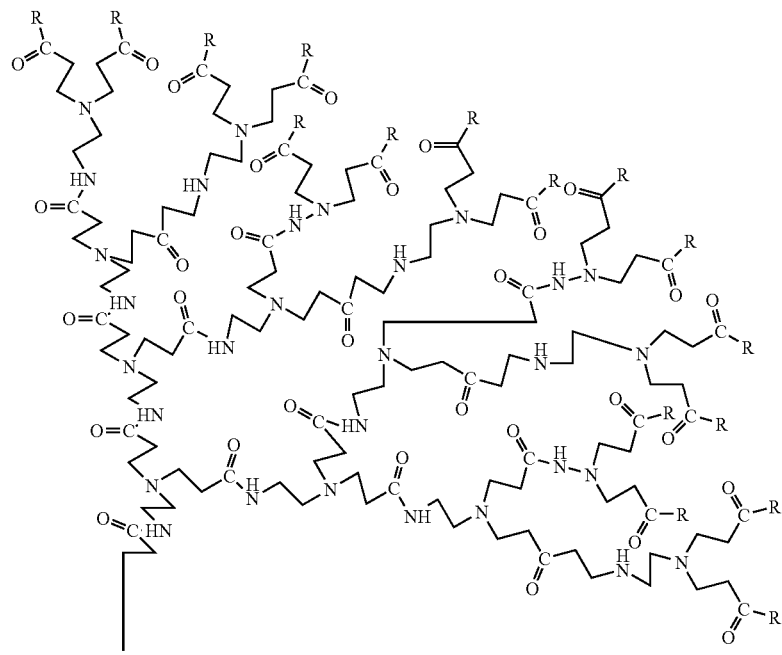
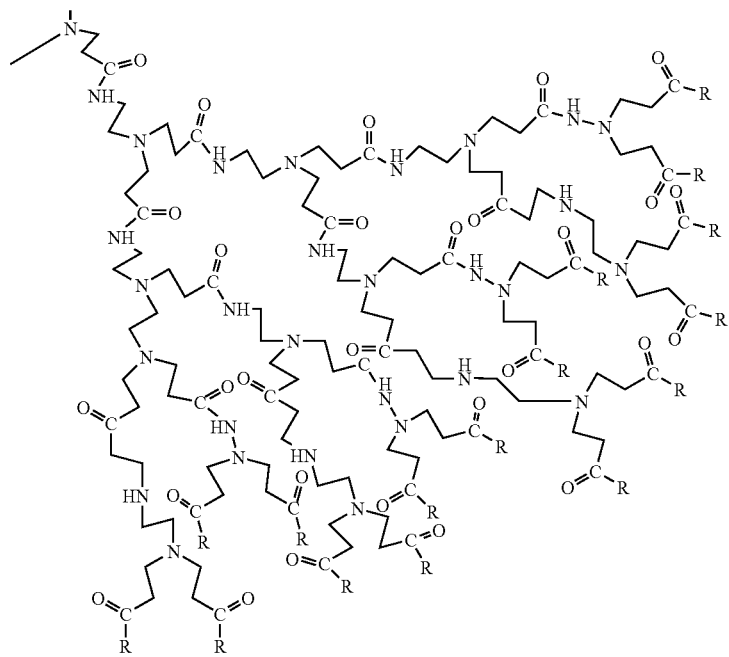
R: ―NH―CH₂CH₂―OH

<Dendritic Branching Molecule (2): Amide Type Dendrimer>
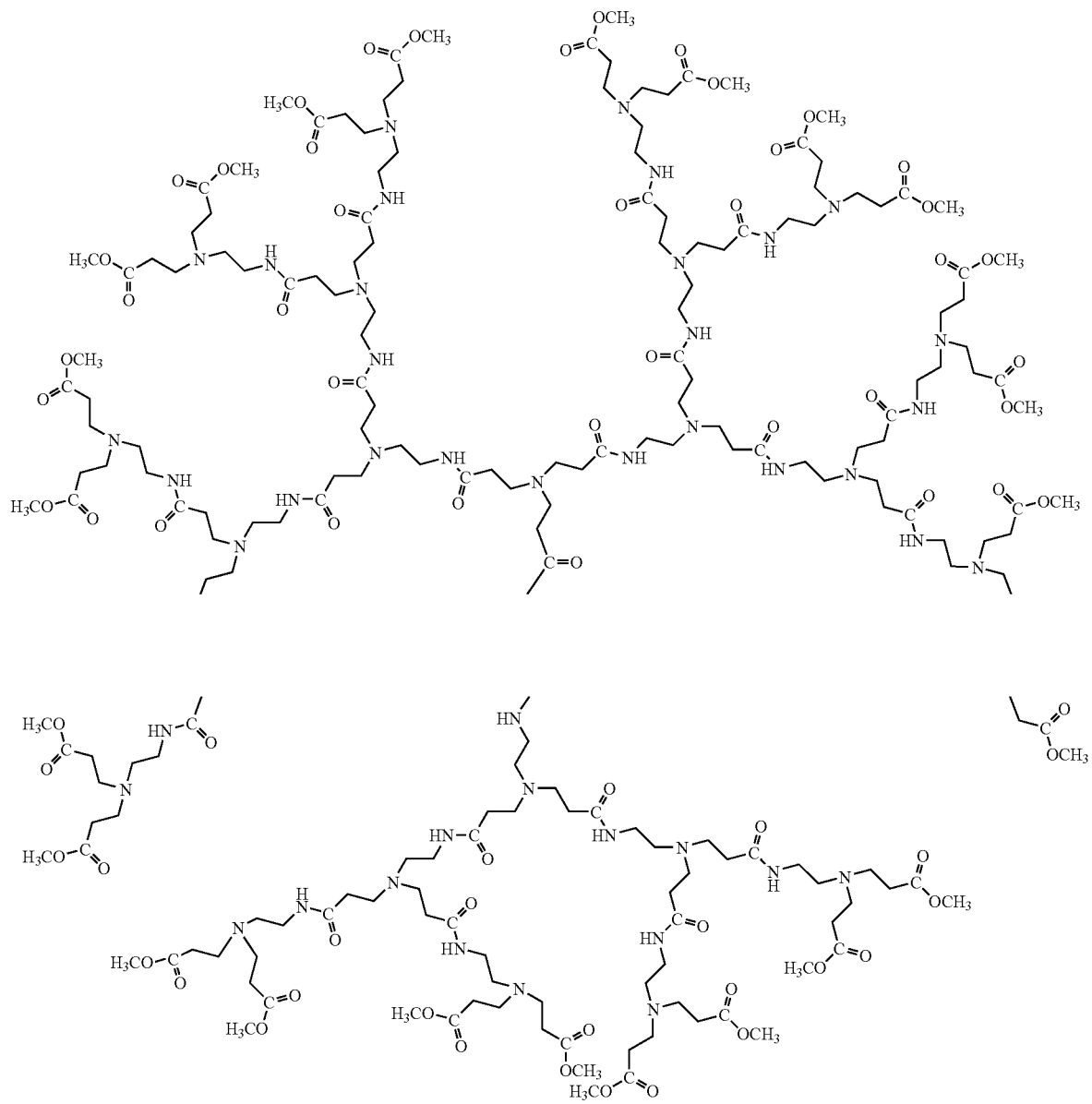

<Dendritic Branching Molecule (3): Amide Type Dendrimer>
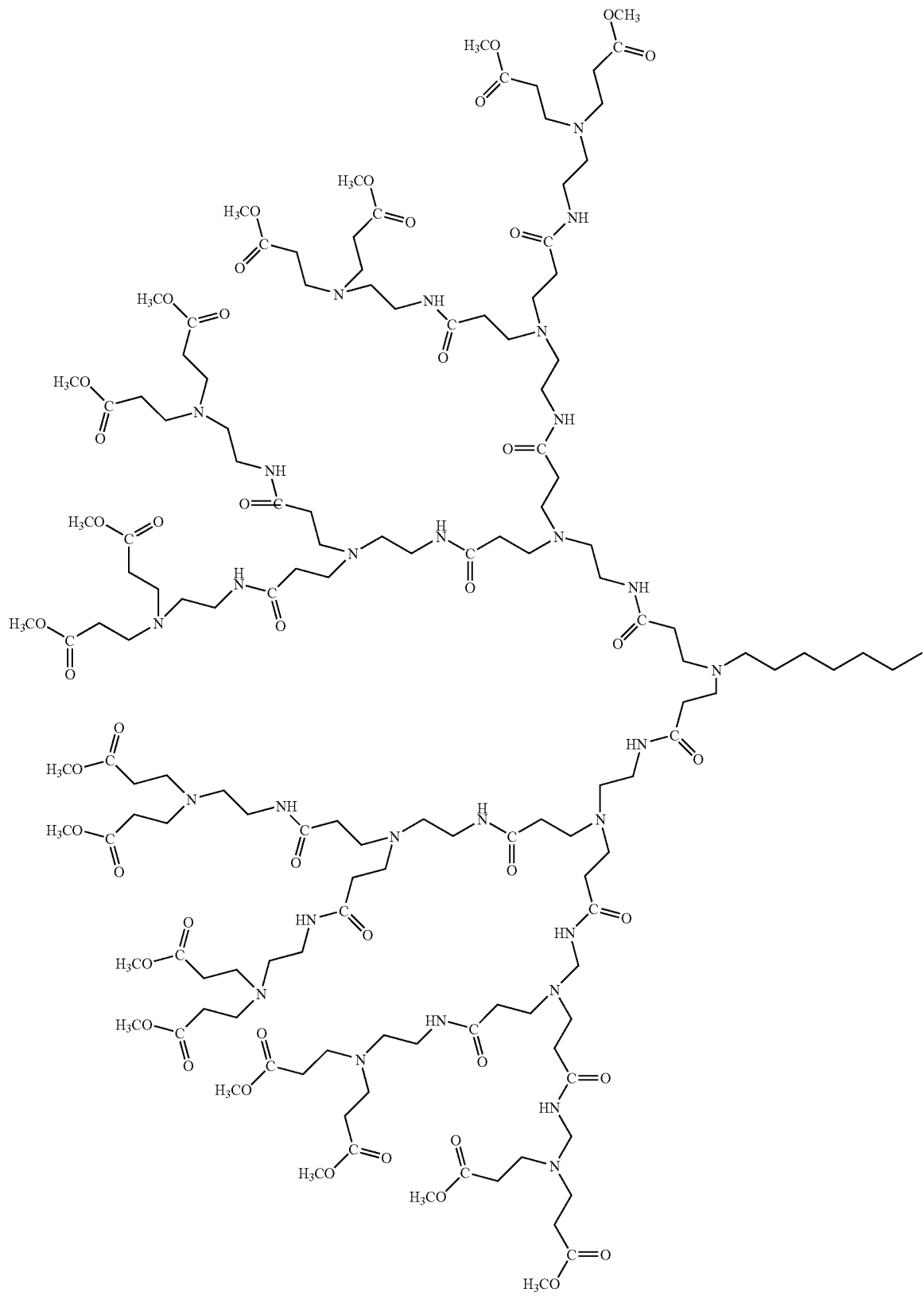

-continued
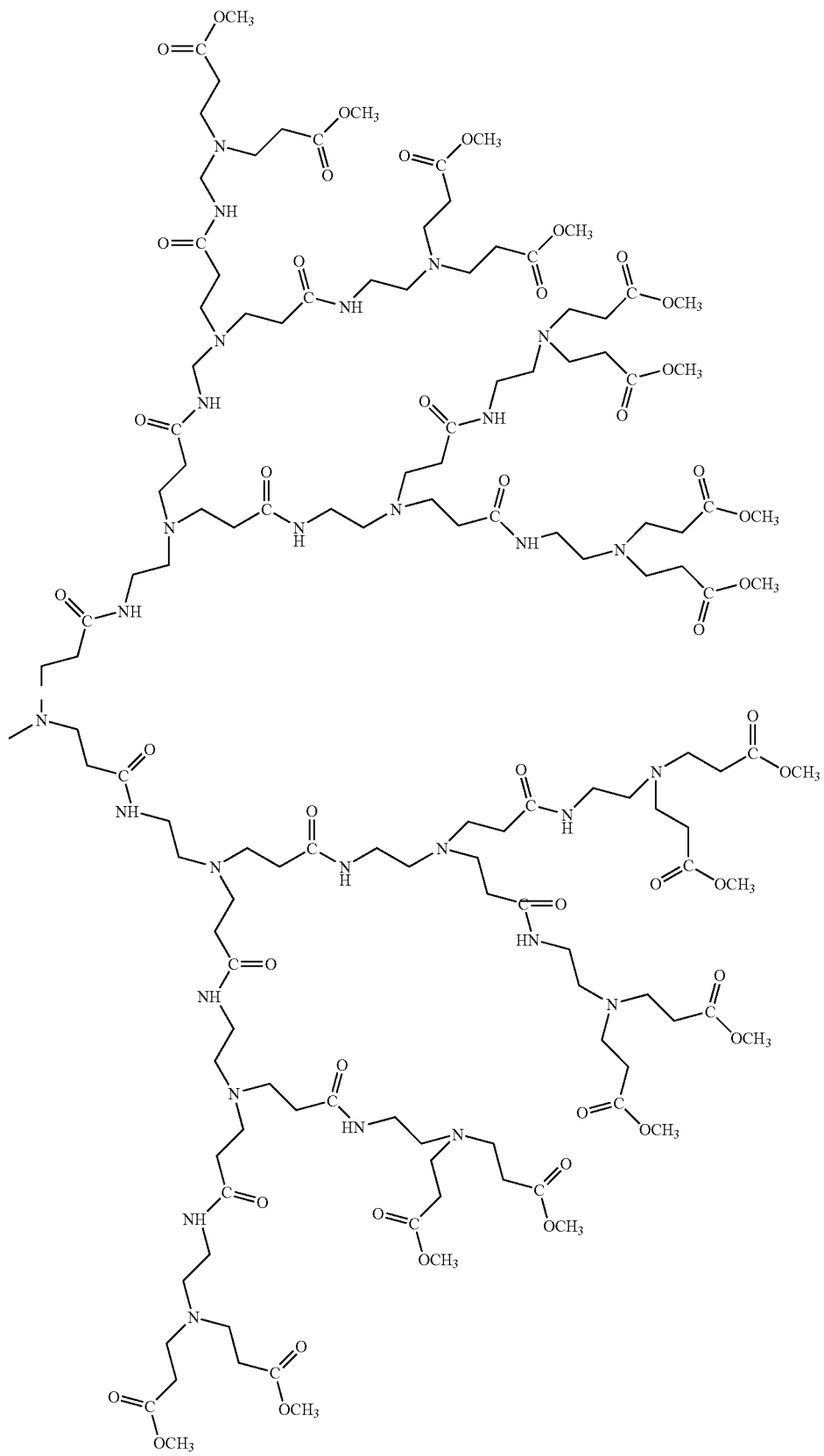

<Dendritic Branching Molecule (4): Amide Type Dendrimer>
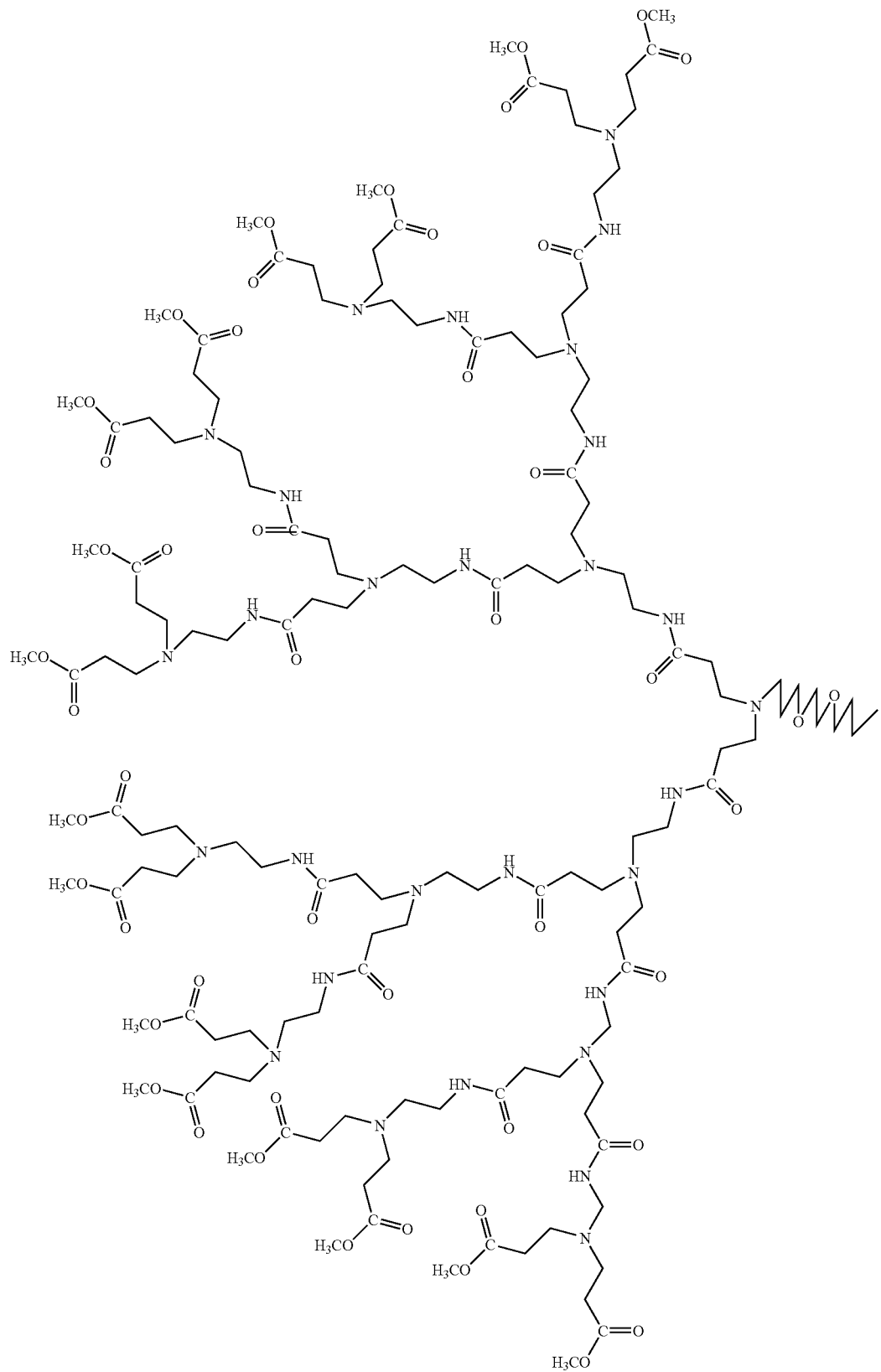

-continued
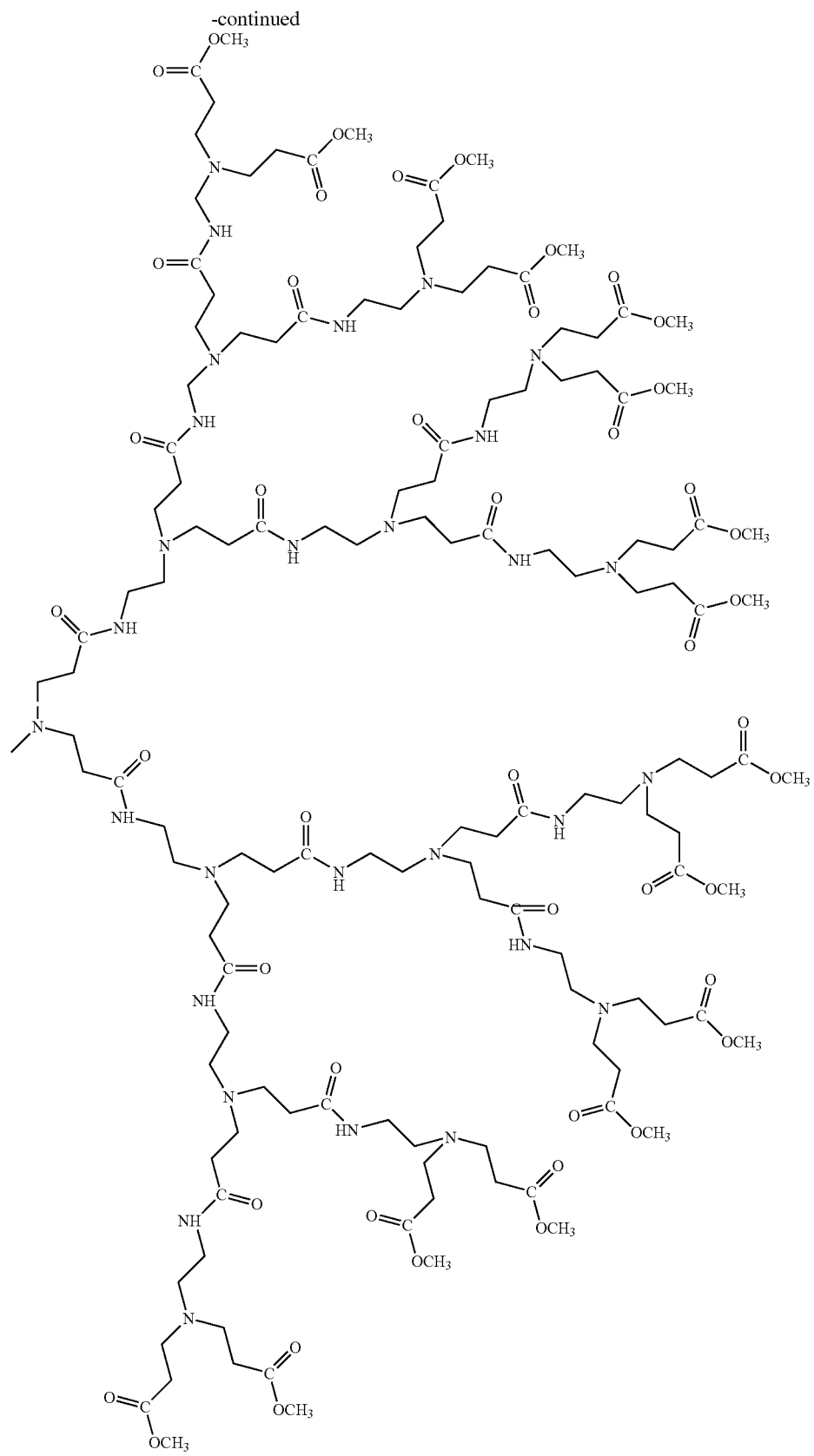

<Dendritic branching molecule (5): Propyleneimine type Dendrimer>
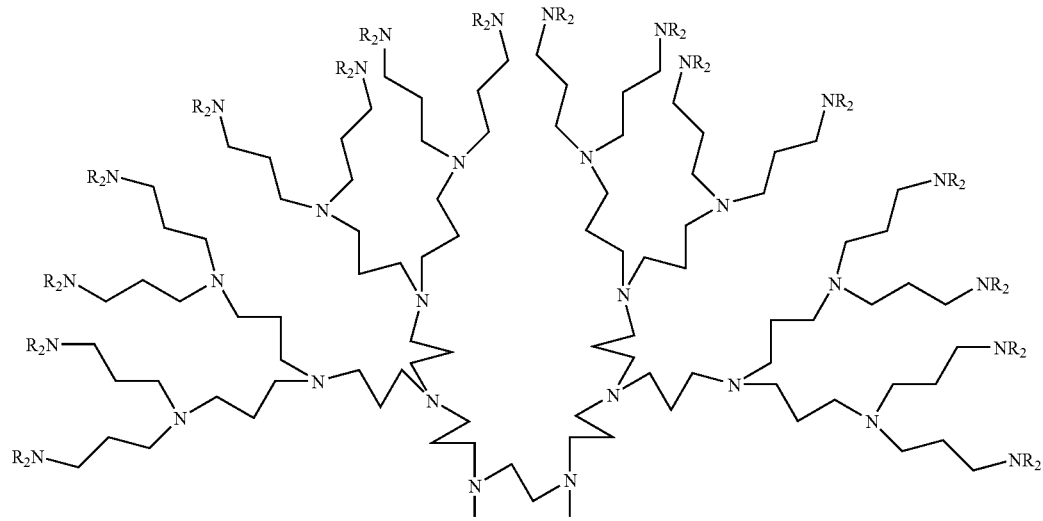
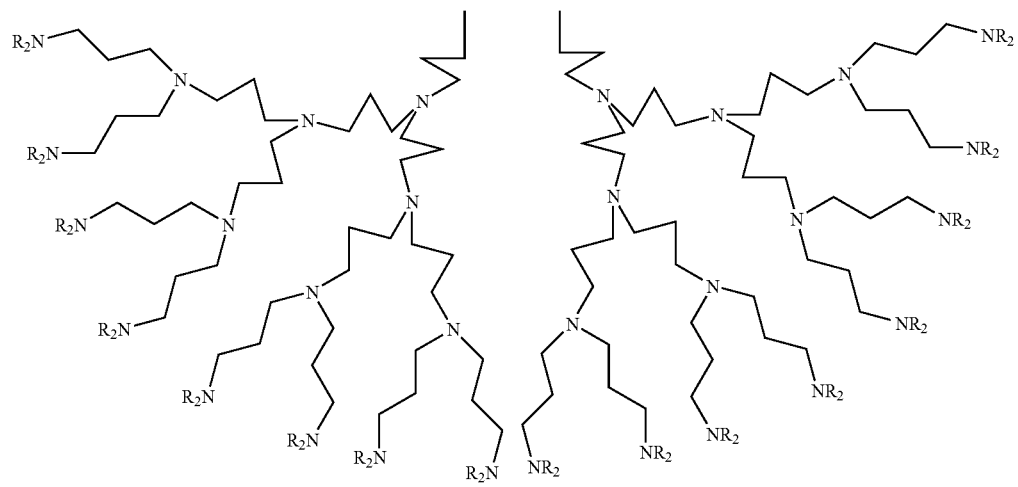
R = 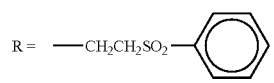

<Dendritic Branching Molecule (6): Propyleneimine Type Dendrimer>
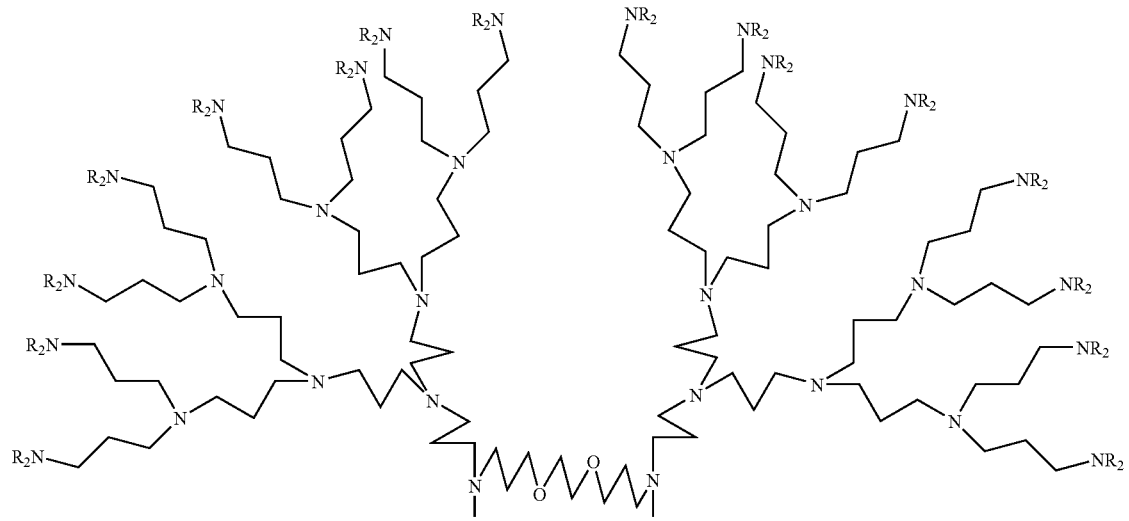
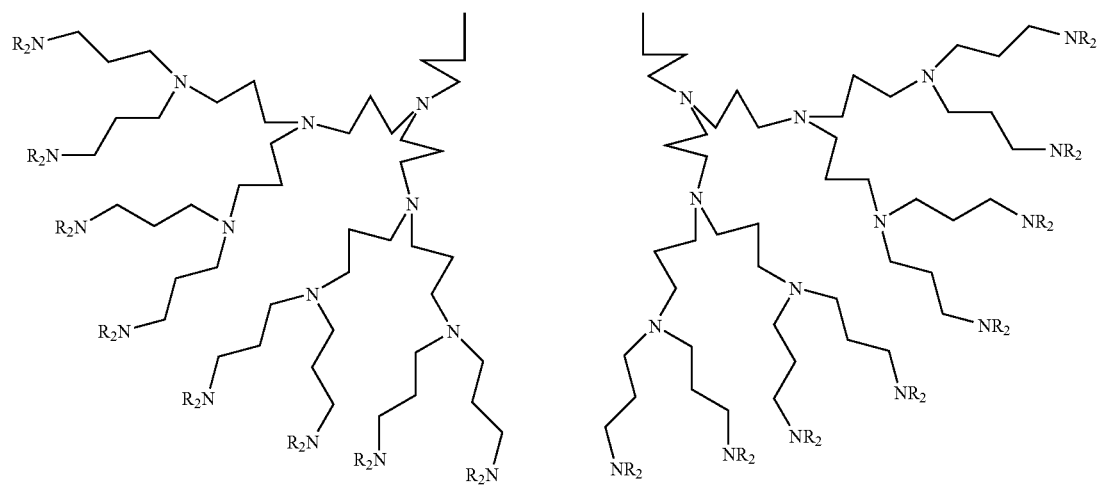
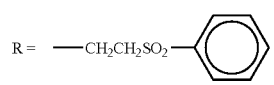

<Dendritic Branching Molecule (7): Propyleneimine Type Dendrimer>
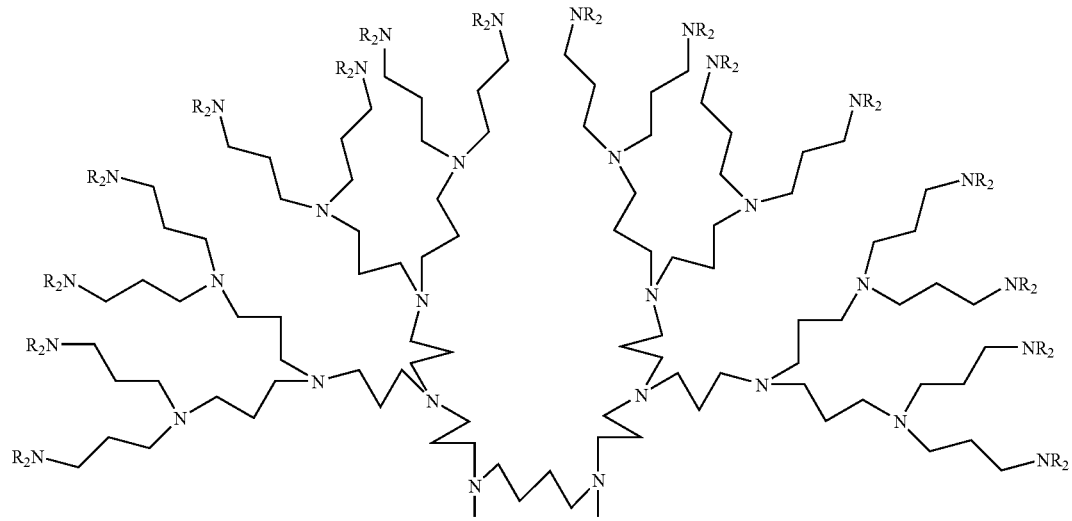
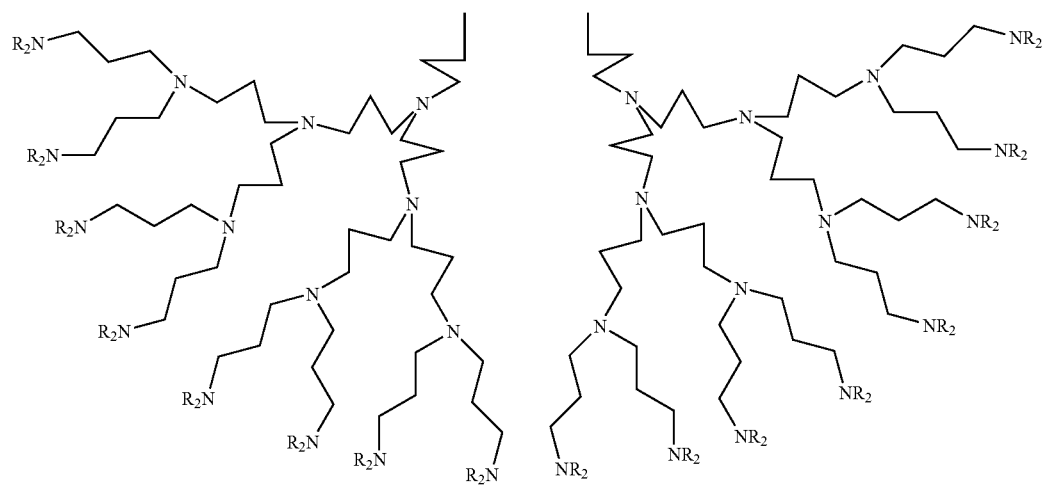
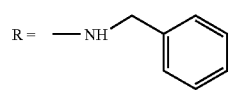

<Dendritic Branching Molecule (8): Methyleneimine Type Dendrimer>
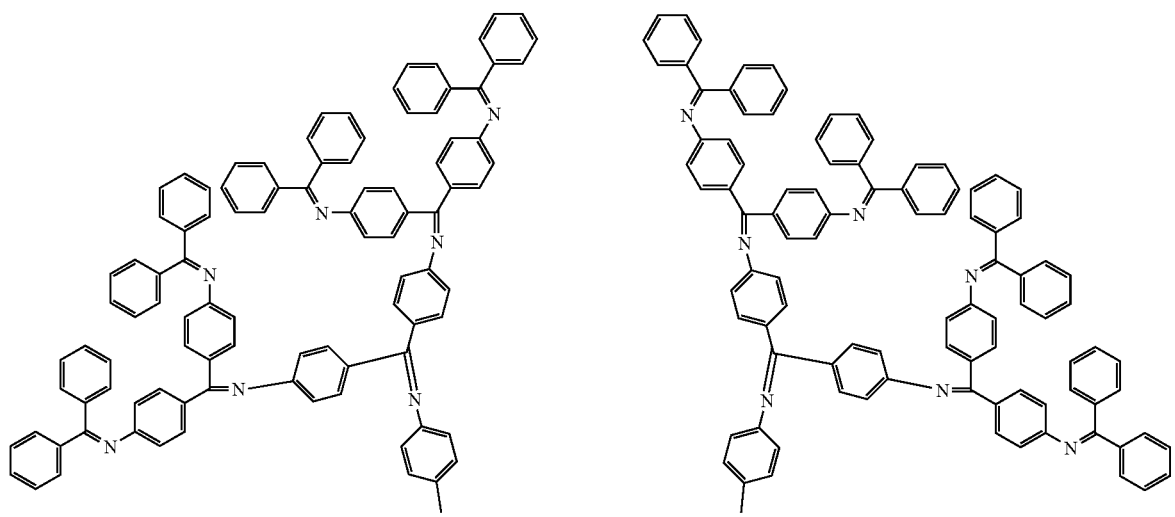
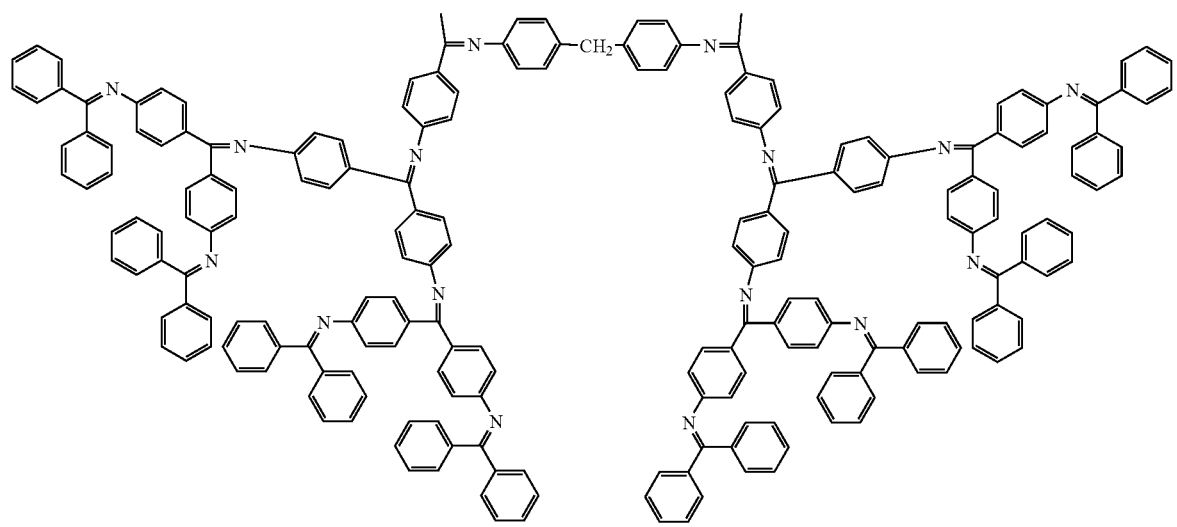
<Dendritic Branching Molecule (9): Dendron>
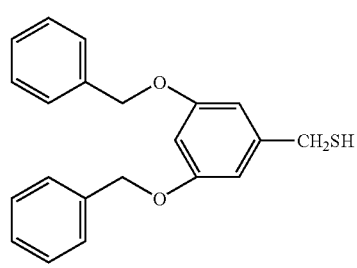
<Dendritic Branching Molecule (10): Dendron>
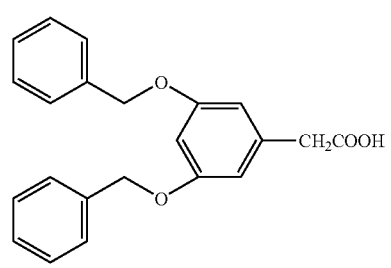

<Dendritic Branching Molecule (11): Dendron>

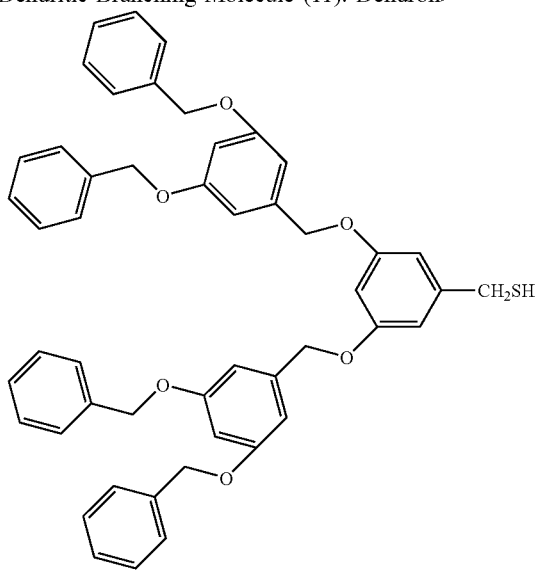

<Dendritic Branching Molecule (12): Dendron>

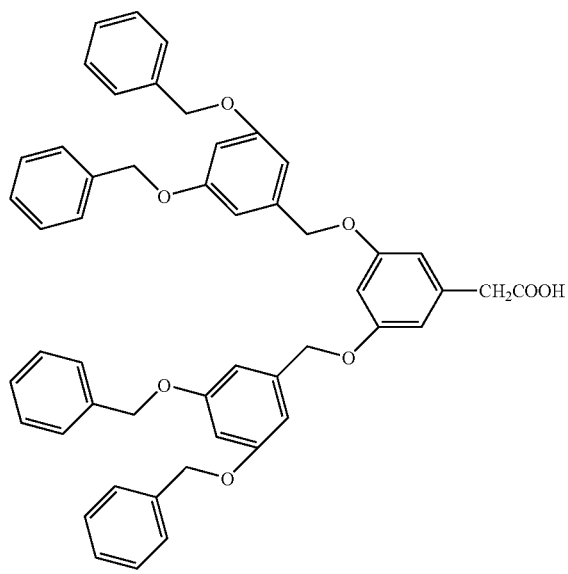

<Dendritic Branching Molecule (13): Hyper-branch Polymer>

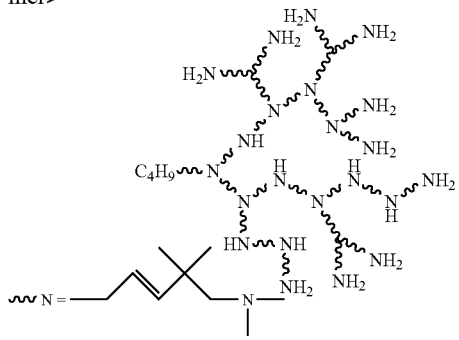

<Dendritic Branching Molecule (14): Hyper-branch Polymer>

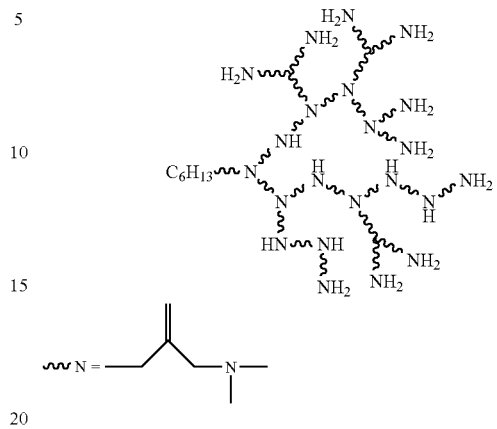

The process for producing a tree-shape, branched polymer having a trimethyleneimine structure as one of the above-described dendritic branching molecules is not limited, and adequately selected for a specific purpose. For example, it can be produced by the following processes.

For example, as disclosed in International Publication No. WO/9314147 and International Publication No. WO/9502008, in the synthesis, a compound containing ammonia and two or more primary amine groups is taken as starting material, this is reacted with acrylonitrile in a cyanoethylation reaction, the nitrile groups are reduced to primary groups using hydrogen or ammonia (G1) in the presence of a catalyst, and subsequently, the cyanoethylation and reduction to primary amine groups are repeated three times (G2→G3→G4). G1 to G4 represent dendrimer generation.

In the process for producing the dendrimer, as starting material, in addition to ammonia, a compound containing at least one type of functional group selected from primary amine, alcohol, phenol, thiol, thiophenol and secondary amine may be used.

Of these dendritic branching molecules, there is no particular limitation on the process for producing the tree-shape, branched polymer containing an amidoamine skeleton which may be selected according to the purpose, examples being the processes shown below.

For example, in the synthesis, a compound containing a primary amine group is taken as starting material, two equivalents of methylacrylate are reacted with this primary amine group (Michael addition reaction) to give a bifunctional methyl ester compound having a nitrogen branch part, then one of the primary amine groups of a diamine compound is reacted with the methylester (ester/transamidation), and the other primary amine group is left (G1). Next, by reacting with two equivalents of methylacrylate, the reaction of one of the primary amine groups of the diamine compound with the methylester leaving the other primary amine group, is repeated three times (G2→G3→G4) (e.g., JP-B No. 07-2840, JP-B No. 07-57735, JP-B No. 07-57736, JP-A No. 07-267879 and JP-A No. 11-140180).

In the process for producing the dendrimer, as starting material, in addition to ammonia, a compound containing at least one type of functional group selected from primary amine, alcohol, phenol, thiol, thiophenol and secondary amine may be used.

The process for producing a tree-shape, branched polymer having a branched, π-conjugate polyarylazomethine structure as one of the above-described dendritic branching molecules is not limited, and adequately selected for a specific purpose. For example, it can be produced by the following process.

First, one equivalent of amino group of 4,4'-diaminobenzophenone is reacted with 2 equivalents of ketone of benzophenone to prepare a product (G2). Next, one equivalent of amino group of 4,4'-diaminobenzophenone is reacted with 2 equivalents of ketone of the product (G2) to prepare a product (G3). Similarly, one equivalent of amino group of 4,4'-diaminobenzophenone is reacted with 2 equivalents of ketone of the product (G3) to prepare a product (G4). Then, one equivalent of a compound having 2 amino groups is reacted with 2 equivalents of the product G4, to synthesize the tree-shape, branched polymer (K. Yamamoto et al, J. Am. Chem. Soc., vol.123, p. 4414, 2001).

The tree-shape, branched polymer having a branched, π-conjugate polyarylazomethine structure preferably has a structure branching from a site other than an aromatic ring.

The dendrimer may be a commercial one, or adequately synthesized one.

A dendron, e.g., that of the dendritic branching molecule (9), can be synthesized by mixing 3,5-bis[3,5-bis(benzoloxy)benziloxy]benzyl bromide, thiourea and a polar solvent with stirring, to which an aqueous solution of sodium hydroxide is added, diluting the resulting mixture with diluted hydrochloric acid at pH 2 to 3, and extracting the dendron with ethyl acetate from the mixture.

The dendron may be a commercial one, or adequately synthesized one.

The process for producing the aforesaid hyper-branch polymer may for example be synthesis by a ring-opening polymerization of a cyclic compound taking a primary amine as a nucleophilic component and using a palladium catalyst, as described in M. Suzuki et al: Macromolecules, Vol. 25, p. 7071 (1992) and Vol. 31, p. 1716 (1998).

The hyper-branch polymer may be a commercial one, or adequately synthesized one.

The focal site (capturing site) in the dendritic branching molecule may be located in a branched chain in the molecule, or at a focal site in the molecule. When the dendritic branching molecule is a polymer, the focal site is preferably located in a branched chain. When it is a dendron, on the other side, the focal site is preferably located at a focal site in the molecule.

The focal site (capturing site) is not limited, and can be adequately selected for a specific purpose. For example, it is preferably a functional group to which the particle precursor can be bound, or functional group which is electrostatically interactive with the precursor.

The bonds by which the functional group can be bound to the particle precursor include coordination, chemical, ionic, and covalent bond.

When the particle precursor is a metallic ion, the functional groups to which the particle precursor can be bound include $NH_3$, $RHN_2$, $N_2H_4$, $H_2O$, $OH-$, $O^{-2}$, $ROH$, $RO-$, $R_2O$, $MeCOO-$, $CO_3^{-2}$, $NO_3-$, $F-$, $PhNH_2$, $C_5H_5N$, $N_2$, $NO_2-$, $SO_3^{-2}$, $Br-$, $H-$, $R-$, $C_2H_4$, $C_4H_6$, $CN-$, $RNC$, $CO$, $SCN-$, $R_3P$, $(RO)_3P$, $R_3As$, $R_2S$, $RSH$, $RS-$, $S_2O_3^{-2}$ and $I-$.

When the particle precursor is a metallic ion, the functional groups which are electrostatically interactive with the precursor include a quaternary ammonium salt, $COO-$, $PO_4^{3-}$ and $PO_4^{2-}$.

The dendritic branching molecule (in particular dendrimer) has preferably no site interactive with the particle precursor other than the focal site. In other words, those dendritic branching molecules having focal sites inside for a particle precursor but no site interactive with the precursor on the surface, such as the molecules (1) to (12), may be used directly. However, those molecules having a number of sites interactive with a precursor other than focal sites are preferably treated to remove these interactive sites other than focal sites by substituting them with a less interactive group (or a group having a lower coordination capacity when the precursor is a metallic ion). In other words, a dendritic branching molecule preferably has a stronger interactivity with a particle precursor at its focal sites than at any site other than the focal site. At the same time, the less interactive substituent preferably has a larger surface area than the dendritic branching molecule itself. For example, a dendritic branching molecule with hydrogen-containing amino group at the branch end is reacted with methyl vinyl ketone, phenyl vinyl ketone, methyl vinyl sulfone, phenyl vinyl sulfone or the like to introduce the less interactive substituent.

The substituents having a lower coordination capacity include phenyl, benzyl and alkyl (which may be substituted or not substituted).

Substituting a dendritic branching molecule with a hard group having a benzene ring, e.g., phenyl or benzyl on the surface, will improve heat resistance, rigidity and light-collecting capacity of the molecule and particle-containing, dendritic branching molecule. They are suitable for those areas which need these properties.

Particle Precursor

Examples of the particle precursors include metallic ion and precursor for semiconducting crystal.

The metallic ion for the precursor is not limited, and may be adequately selected fro a specific purpose. The preferable ones include Group 3A, 4A, 5A, 6A, 7A, 8, 1B, 2B, 3B and 6B elements in the periodic table. Of these, more preferable ones are Ti, Fe, Co, Ni, Zr, Mo, Ru, Rh, Ag, Cd, Sn, Ir, Pt, Au, Pb and Bi. They may be used either individually or in combination.

The particle precursor is preferably incorporated at a content in such a way that number of the precursor is equal to or less than number of focal sites of the dendritic branching molecules, when the molecule has focal sites in the molecular chain, without needing a step for removing the excessive particle precursor which is not captured by the dendritic branching molecule.

When the incorporated particle precursor outnumbers focal sites of the dendritic branching molecule, it is preferable to transform the particle precursor captured by the focal sites, after removing the excessive particle precursor which is not captured by the dendritic branching molecule. In this case, as many the seed particles as the focal sites can be formed, which is preferable for producing the particles substantially uniform in size and composition. Incorporating as many the particle precursor as focal sites of the dendritic branching molecule is also preferable for producing the particles substantially uniform in size and composition.

Means for totally capturing the particle precursor by the dendritic branching molecule at the focal sites include, when the molecule has one or more focal sites in the branch, (1) incorporation as may the precursor as the focal sites in the dendritic branching molecule, and (2) incorporation of the precursor in excess of the focal sites, and then removing (e.g., by dialysis) of the excessive precursor.

One precursor may be captured by one focal site, or by 2 or more sites.

<Particle Forming Step>

The particle forming step transforms the particle precursor captured by the dendritic branching molecule into the particle.

The process for transforming the particle precursor into the particle is not limited, so long as it can perform the transformation, and may be adequately selected for a specific purpose. For example, the process is preferably based on reduction, when the precursor is a metallic ion.

The transformation is preferably achieved in the presence of a reagent. The reagent is not limited, so long as it helps transform the particle precursor into the particle, and may be adequately selected for a specific purpose. Examples of the reagent include a reducing agent and specific reagent.

The reducing agent or specific reagent is not limited, and may be adequately selected for a specific purpose. Examples of these reducing agent and specific reagent include $H_2$ gas, sodium borohydride, hydrazine, ascorbic acid, and tetraoctyl ammonium bromide (TOAB) as an interlaminar transfer agent for the particle precursor (metallic ion).

The transformation is achieved by simultaneously incorporating a liquid containing the dendritic branching molecules which capture the particle precursor and liquid containing a reducing reagent dropwise to form the mixture. This process is preferable for producing the nano-particles having a sharp size distribution. It is preferable that these liquids are almost the same in quantity. They are preferably mixed with each other under heating, normally at 15 to 90° C.

The container in which these liquids are put dropwise is not limited, and may be adequately selected for a specific purpose. Examples of the container include syringe, a combination of syringe and tube, Y-shaped microtube and microreactor.

These liquids may be sent manually, or by a syringe pump or the like. They are preferably sent continuously or intermittently, the latter being particularly preferable for improving mixing efficiency.

Figure 4:
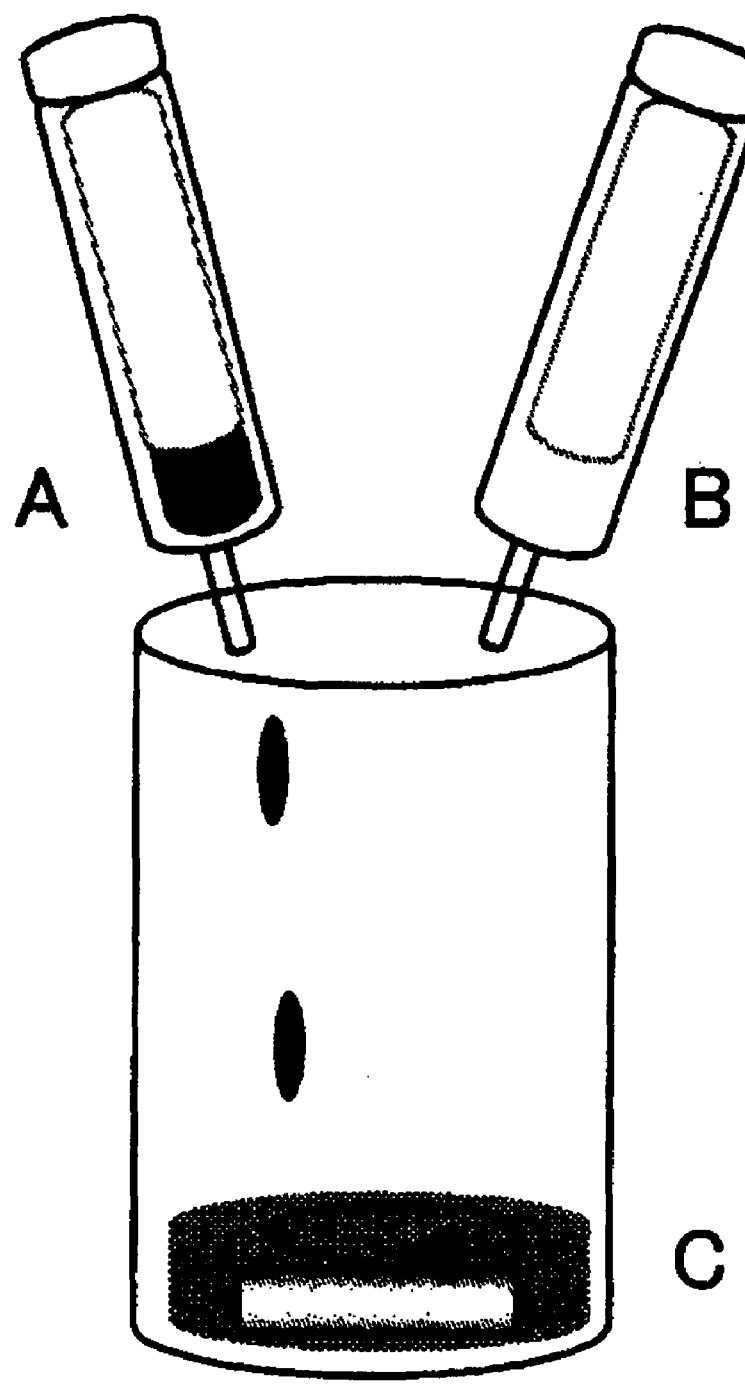
FIG. 4 outlines a procedure for simultaneously incorporating a dendrimer solution in which a metal complex is formed and reducing solution.

Some of the processes for mixing these liquids are described in detail. Referring to FIG. 4, a liquid containing the dendritic branching molecules which capture the particle precursor is put in the syringe A and liquid containing a reducing reagent in the syringe B, and they are simultaneously pressed downwards to go drop by drop at a fixed rate into a beaker, in which they are stirred. They may be sent manually, or by a syringe pump or the like normally at 0.05 to 10 mL/minute. In the system shown in FIG. 4, each liquid may be heated through a tube attached to the syringe end.

Figure 5:
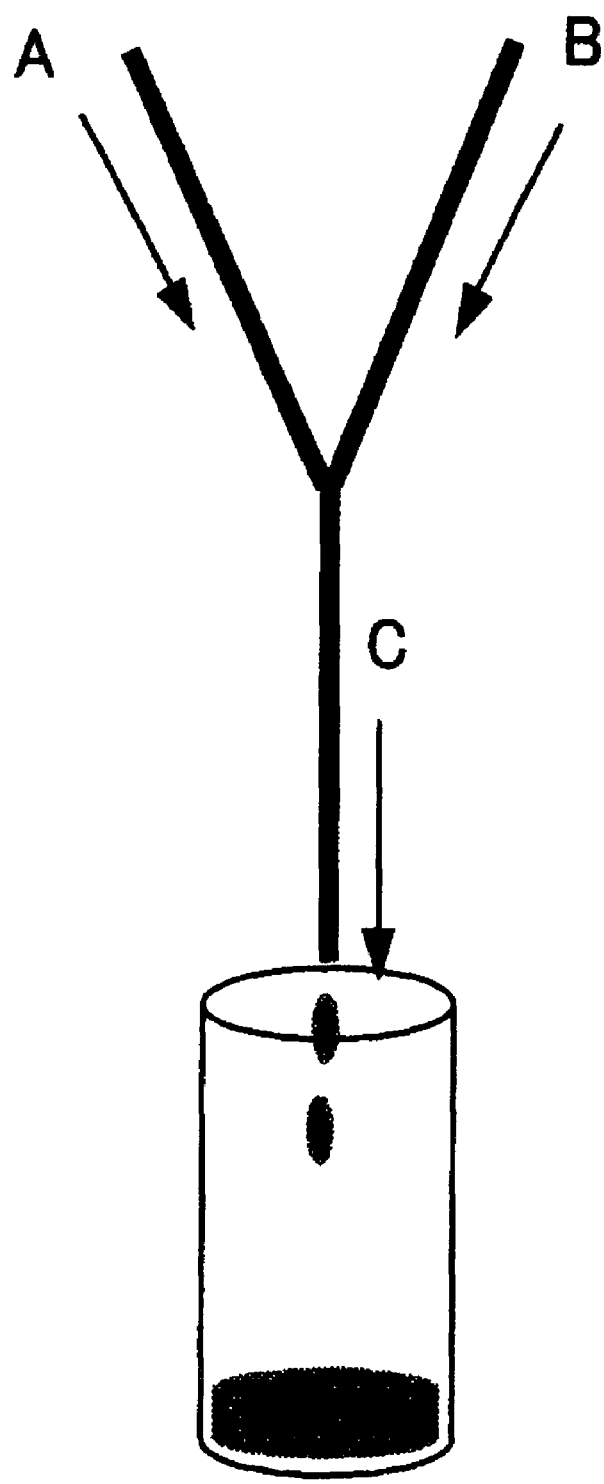
FIG. 5 outlines another procedure for simultaneously incorporating a dendrimer solution in which a metal complex is formed and reducing solution.

These liquids may be simultaneously sent dropwise by a tube with Y-shaped passage, shown in FIG. 5, where a liquid containing the dendritic branching molecules which capture the particle precursor is sent in the direction A and liquid containing a reducing reagent in the direction B at a fixed rate into a beaker, in which they are stirred. They may be sent manually, or by a syringe pump or the like, and continuously or intermittently (alternately), the latter being more preferable for improving mixing efficiency.

The tube with Y-shaped passage, shown in FIG. 5, may be replaced by a substrate of metal, glass, silicon or the like provided with a Y-shaped passage thereon. These liquid may be heated while being sent from the passage A or B to passage C, normally preferably at 15 to 90° C. They may be sent normally preferably at 0.05 to 10 mL/minute.

Particles

The particles may be inorganic or organic particles, or the like, of which inorganic particles are more preferable.

The inorganic particles are not limited, and may be adequately selected for a specific purpose. They may be of metal, semiconducting crystal, metallic chalcogenide, metal halide or the like. More specifically, they may be of gold, platinum, iron, gold/platinum alloy and silver halide, among others.

The platinum alloys include alloys of platinum with one or more elements selected from the group consisting of Sc, Y, Ti, Zr, V, Nb, Fe, Co, Ni, Ru, Rh, Pd, Os, Ir, and a lanthanoide and actinoid element.

The particles of semiconducting crystal are not limited, and may be adequately selected for a specific purpose. They include Group 14 elements in the periodic table, e.g., C, Si, Ge and Sn; Group 15 elements, e.g., P (black phosphorus); Group 16 elements, Se and Te; compounds of 2 or more Group 14 elements, e.g., SiC; compounds of Group 14 and Group 16 element, e.g., $SnO_2$, $Sn(II)Sn(IV)S_3$, $SnS_2$, SnS, SnSe, SnTe, PbS, PbSe and PbTe; compounds of Group 13 and Group 15 element, e.g., BN, BP, BAs, AlN, AlP, AlAs, AlSb, GaN, GaP, GaAs, GaSb, InN, InP, InAs and InSb (or compound semiconductors of Group 3 and 5element); compounds of Group 13 and Group 16 element, e.g., $Al_2S_3$, $Al_2Se_3$, $Ga_2S_3$, $Ga_2Se_3$, $Ga_2Te_3$, $In_2O_3$, $In_2S_3$, $In_2Se_3$ and $In_2Te_3$; compounds of Group 13 and Group 17 element, e.g., TlCl, TlBr and TlI; compounds of Group 12 and Group 16 element, e.g., ZnO, ZnS, ZnSe, ZnTe, CdO, CdS, CdSe, CdTe, HgS, HgSe and HgTe (or compound semiconductors of Group 2 and 4element); compounds of Group 15 and Group 16 element, e.g., $As_2S_3$, $As_2Se_3$, $As_2Te_3$, $Sb_2S_3$, $Sb_2Se_3$, $Sb_2Te_3$, $Bi_2S_3$, $Bi_2Se_3$ and $Bi_2T_3$; compounds of Group 11 and Group 16 element, e.g., $Cu_2O$ and $Cu_2Se$; compounds of Group 11 and Group 17 element, e.g., CuCl, CuBr, CuI, AgCl and AgBr; compounds of Group 10 and Group 16 element, e.g., NiO; compounds of Group 9 and Group 16 element, e.g., CoO and CoS; compounds of Group 8 and Group 16 element, e.g., iron oxides (e.g., $Fe_3O_4$) and FeS; compounds of Group 7 and Group 16 element, e.g., MnO; compounds of Group 6 and Group 16 element, e.g., $MoS_2$ and $WO_2$; compounds of Group 5 and Group 16 element, e.g., VO, $VO_2$, $Ta_2O_5$; compounds of Group 4 and Group 16 element, e.g., titanium oxides (e.g., $TiO_2$, $Ti_2O_5$, $Ti_2O_3$ and $Ti_5O_9$, where the crystalline form may be rutile, rutile/anatase mixed or anatase) and $ZrO_2$; compounds of Group 2 and Group 16 element, e.g., MgS and MgSe; chalcogen spinels, e.g., $CdCr_2O_4$, $CdCr_2Se_4$, $CuCr_2S_4$ and $HgCr_2Se_4$; and $BaTiO_3$. The other semiconducting crystals useful for the present invention include semiconducting clusters, e.g., $(BN)_{75}(BF_2)_{15}F_{15}$ disclosed by G. S. Schmid et al, Adv., Mater., vol.4, p. 494, 1991; and $Cu_{146}Se_{73}$ (triethylphosphine)$_{22}$, disclosed by D. Fenske et al, Angew. Chem. Int. Ed. Engl., vol. 29, p. 1452, 1990.

Of these, the more preferable ones viewed from practicality are compounds of Group 14 and Group 16 element, e.g., $SnO_2$, $SnS_2$, SnS, SnSe, SnTe, PbS, PbSe and PbTe; compound semiconductors of Group 3 and 5element, e.g., GaN, GaP, GaAs, GaSb, InN, InP, InAs and InSb; compounds of Group 13 and Group 16 element, e.g., $Ga_2O_3$, $Ga_2S_3$, $Ga_2Se_3$, $Ga_2Te_3$, $In_2O_3$, $In_2S_3$, $In_2Se_3$ and $In_2Te_3$; compound semiconductors of Group 2 and 4element, e.g., ZnO, ZnS, ZnSe, ZnTe, CdO, CdS, CdSe, CdTe, HgO, HgS, HgSe and HgTe; compounds of Group 15 and Group 16 element, e.g., $As_2O_3$, $As_2S_3$, $As_2Se_3$, $As_2Te_3$, $Sb_2O_3$, $Sb_2S_3$, $Sb_2Se_3$, $Sb_2Te_3$, $Bi_2O_3$, $Bi_2S_3$, $Bi_2Se_3$ and $Bi_2Te_3$; compounds of Group 8 and Group 16 element, e.g., iron oxides (e.g., $Fe_3O_4$) and FeS; compounds of Group 4 and Group 16 element, e.g., titanium oxides and $ZrO_2$; and compounds of Group 2 and Group 16 element, e.g., MgS and MgSe.

The still more preferable ones are $SnO_2$, GaN, GaP, $In_2O_3$, InN, InP, $Ga_2O_3$, $Ga_2S_3$, $In_2O_3$, $In_2S_3$, ZnO, ZnS, CdO, CdS, titanium oxides, $ZrO_2$ and MgS for their high refractive index, and low environmental loads and safety to organisms. The still more preferable ones are $SnO_2$, $In_2O_3$, ZnO, ZnS, titanium oxides and $ZrO_2$. The particularly preferable ones are ZnO and titanium oxides.

The more preferable ones viewed from light-emitting capacity are compound semiconductors of Group 2 and 4 element, e.g., ZnO, ZnS, ZnSe, ZnTe, CdO, CdS and CdSe; and the still more preferable ones are ZnSe, CdS and CdSe.

The semiconducting compounds described above may contain a dopant, as required. The dopants useful for the present invention include Al, Mn, Cu, Zn, Ag, Cl, Ce, Eu, Th and Er.

Size of the particles produced by the process of the present invention for producing nano-particles is not limited, and may be adequately selected for a specific purpose. However, it is preferably 0.1 to 500 nm, more preferably 0.3 to 100 nm, still more preferably 0.3 to 10 nm. Size distribution of the particles is preferably 0 to 200 nm, more preferably 0 to 100 nm. The particle size means diameter when the particle is spherical, and long side when it is rod-shaped. When a dendron is used as the tree-shape, branched polymer, the composite nano-particles (with the dendron on the surface) having a small size of 0.1 to 10 nm and sharp size distribution of 0.0 to 10 nm can be produced.

<Particle Growing Step>

The particle growing step is for growing the particles prepared in the particle forming step, which serve as the seed.

The process for the particle growing step is not limited, so long as it can grow the particles prepared in the particle forming step, and may be adequately selected for a specific purpose. However, the particles prepared in the particle forming step are preferably grown by incorporating a liquid containing a particle precursor to transform the precursor into the particles after it is captured by the dendritic branching molecules.

The particle growing step is preferably carried out at least once. It can be carried out as many cycles as required in consideration of number of the dendritic branching molecules available for capturing the particle precursor and target size of the nano-particles, among others.

The particle precursor for the particle growing step may be the same as, or different from, that for the particle precursor capturing step. When it is the same as that for the particle precursor capturing step, the particles prepared in the particle forming step are grown as the seed to prepare the particles of the same composition. When it is different, on the other hand, the particles prepared in the particle forming step are grown as the core, which is coated with a shell formed in the particle growing step to produce the core-shell structure having a composition and function in the core different from those in the shell. In this case, one or more types of particle precursors may be charged to the particle growing step while being carried by a liquid. When 2 or more types are charged, the shell can have a composition composed of these precursors. Moreover, the liquid containing the particle precursor(s) may be changed to another liquid once or more during the particle growing step. When it is changed 2 or more times, a plurality of shell layers of different composition can be formed. A liquid containing 2 or more types of particle precursors may be changed to another alternately or consecutively. In this case, the different shell layers of composition changing in the above order can be formed. Moreover, the liquid may be changed by another liquid containing a particle precursor which is the same or different from the one for the particle precursor capturing step. The different shell layers of composition changing in the above order can be formed also in this case.

One example of the process for forming the particles of core-shell structure is described. After the particles (seed particles) are formed in the particle forming step, the same particle precursor type as used in the particle precursor capturing step is charged to the particle growing step, while being carried by a liquid, cyclically until the core is grown to a given size in this step. Then, a liquid containing a particle precursor different from that for the particle precursor capturing step is charged to the particle growing step cyclically until the shell covering the core is grown to a given size.

When the particles of core-shell structure with a small core are to be formed, a liquid containing a particle precursor different from that for the particle precursor capturing step may be charged from the first cycle of the tree-shape, branched polymer cyclically until the particles are grown to a given size.

The particle of core-shell structure exhibits a function on the surface different from that inside. Examples of the different functions are the surface functions characteristically different from a function inside, e.g., catalytic function on the surface or protective function for the particle inside.

The particle precursor is preferably incorporated in the particle growing step at a content in such a way that number of the precursor is equal to or less than number of focal sites of the dendritic branching molecule, when the molecule has focal sites in the molecular chain. This can efficiently grow the particle, because it can dispense with a step for removing the excessive particle precursor which is not captured by the dendritic branching molecule.

When the incorporated particle precursor outnumbers focal sites of the dendritic branching molecule, it is preferable to transform the particle precursor captured by the focal sites, after removing the excessive particle precursor which is not captured by the dendritic branching molecule. In this case, as many the seed particles as the focal sites can be formed, which is preferable for producing the particles substantially uniform in size and composition. Incorporating as many the particle precursor as focal sites of the dendritic branching molecule is also preferable for producing the particles substantially uniform in size and composition.

The tree-shape, branched polymer molecule which captures the particle precursor in the particle forming step at the focal site can further capture the particle precursor in the particle growing step at the same focal site. Therefore, the particles can be further grown by adding a liquid containing the particle precursor again to the tree-shape, branched polymer containing the seed particles to capture the precursor at the focal site which has already captured the precursor and by transforming the precursor into the particle.

Size of the grown particles is not limited, and may be adequately selected for a specific purpose. However, it is preferably 0.1 to 500 nm, more preferably 0.1 to 200 nm. Size distribution of the grown particles is preferably 0 to 200 nm, more preferably 0 to 100 nm. The particle size means diameter when the particle is spherical, and long side when it is rod-shaped (elliptic).

The process of the present invention for producing nano-particles captures a particle precursor by a dendritic branching molecule in the particle precursor capturing step. This step can produce the substantially monodisperse nano-particles each carrying the dendritic branching molecule, because the dendritic branching molecule has substantially uniform focal sites to help selectively transform the particle precursor it captures into each particle. The particle growing step grows the nano-particles prepared in the preceding particle forming step as the seed. The monodisperse nano-particles substantially uniform in, and freely controllable in, size and composition can be efficiently produced at low cost by repeating the particle growing step to grow the particles.

The substantially uniform particles (or seed particles) prepared by the process of the present invention as the starting material can be grown into the larger, substantially uniform particles by depositing thereon a metal, semiconducting crystal, metallic chalcogenide or metal halide under the conditions not to form new nuclei. In this case, size of the final particles is neither limited to that of the dendritic branching molecule nor to the nano scale, but can be extended to several microns.

The nano-particles produced by the process of the present invention for producing nano-particles are the monodisperse particles uniform in size and substantially uniform in composition. As such, they are applicable to all areas which use nano-particles of metal, semiconducting crystal, metallic chalcogenide or metal halide, in particular to those areas which can have improved performance by use of monodisperse particles. These areas include, but not limited to, materials for high-density recording materials, catalysts, fuel cells, silver halide photoconductor materials, electrophotography, antidazzling films, and optical films, e.g., light-guiding plates.

Nano-particles

The nano-particles of the present invention are produced by the process of the present invention for producing nano-particles.

The nano-particles of the present invention are the monodisperse particles uniform in size and substantially uniform in composition.

Size of the particles is not limited, but preferably 0.1 to 500 nm. Size distribution of the particles is preferably 0 to 200 nm. The particle size means diameter when the particle is spherical, and long side when it is rod-shaped.

Use of a dendron as the tree-shape, branched polymer gives the composite nano-particles (with the dendron on the surface), which can be reduced in size to 0.1 to 10 nm and narrowed in size distribution to 0.0 to 10 nm. As such, they are applicable to all areas which use nano-particles of metal, semiconducting crystal, metallic chalcogenide or metal halide, in particular to those areas which can have improved performance by use of monodisperse particles. These areas include, but not limited to, materials for high-density recording materials, catalysts, fuel cells, silver halide photoconductor materials, electrophotography, antidazzling films, and optical films, e.g., light-guiding plates.

The present invention is described in more detail by EXAMPLES, which by no means limit the present invention.

EXAMPLE 1

Preparation of Metallic Ion-dendrimer Complex

First, 10.0 mL of a 15 mM aqueous solution of $K_2[PtCl_4]$ ($15.0 \times 10^{-5}$ mol) was transferred to a 20 mL dropping funnel using a 50 mL Erlenmeyer flask. Next, 5.0 mL of a 0.5 mM aqueous solution of dendrimer [Starburst® (polyamine-based dendrimer (PAMAM), supplied by Aldrich, fourth generation, having 64 OH groups on the surface)] was transferred to another 50 mL Erlenmeyer flask, to which a platinum ion solution was added dropwise at room temperature in 5 minutes with stirring by a magnetic stirrer, and the mixture was stirred at 40° C. for 4 hours.

The resulting platinum ion-dendrimer complex/water was analyzed by elementary analysis (Perkin Elmer's 2400) for atomic nitrogen and atomic absorption spectrometer (Hitachi's Z5010) for platinum ion, to confirm that the platinum ion/nitrogen atomic ratio was 60/62.

The resulting solution was analyzed for the UV spectral pattern, to confirm that it had a new absorption at 260 nm which the aqueous solutions of the polyamideamine-based dendrimer and $K_2[PtCl_4]$ lacked.

The reaction solution was spread on a washed PET base and dried to prepare the sample, which was analyzed for ESCA(Electron Spectroscopy for Chemical Analysis) to confirm that the chemical shift of Pt-$4f_{7/2}$ of the aqueous solution of $K_2[PtCl_4]$ was changed from 73.0 to 72.5 eV. It was also confirmed that the chemical shift of N-1s of the aqueous solution of the polyamideamine-based dendrimer was changed from 398.4 to 399.3 eV.

Preparation of the Seed-containing Dendrimer 1a

A dialyzed platinum ion-dendrimer complex was bubbled with a nitrogen gas for 3 hours, to which $75.0 \times 10^{-5}$ mol of sodium borohydride was added little by little, and the mixture was allowed to stand at room temperature for 16 hours, while the nitrogen atmosphere was maintained. Then, the reaction solution was dialyzed in a cellulose tube (supplied by VISKASE) for dialysis with 300 mL of deionized water twice a day, to prepare the seed-containing dendrimer 1a.

The resulting seed-containing dendrimer 1a was analyzed by elementary analysis (Perkin Elmer's 2400) for atomic nitrogen and atomic absorption spectrometer (Hitachi's Z5010) for platinum ion, to confirm that the platinum ion/nitrogen atomic ratio was 60/62. Size of the seed-containing dendrimer 1a particles was observed by a transmission electron microscope (TEM), and the results indicated that the particles were uniform in size, having a diameter of 1.3 nm.

The reaction solution was spread on a washed PET base and dried to prepare the sample, which was analyzed for ESCA(Electron Spectroscopy for Chemical Analysis) to confirm that the chemical shift of Pt-$4f_{7/2}$ of the aqueous solution of $K_2[PtCl_4]$ was further changed 71.3 eV, which corresponds to the chemical shift of metallic Pt. It was also confirmed that the chemical shift of N-1s of the aqueous solution of the polyamideamine-based dendrimer was returned back to 398.4 eV.

Particle Growing Step

First, $6.0 \times 10^{-5}$ mol of an aqueous solution of $K_2[PtCl_4]$ was added dropwise to an aqueous solution containing the seed-containing dendrimer 1a at $1 \times 10^{-6}$ mol (as dendrimer) at room temperature in 5 minutes with stirring by a magnetic stirrer, and the mixture was stirred at 40° C. for 4 hours. Then, $3.0 \times 10^{-4}$ mol of sodium borohydride was added little by little in a nitrogen atmosphere, and the mixture was allowed to stand at room temperature for 16 hours, to prepare the seed-containing dendrimer 1b.

The particle-containing dendrimer 1b took a structure illustrated in FIG. 1. It was analyzed by elementary analysis (Perkin Elmer's 2400) for atomic nitrogen and atomic absorption spectrometer (Hitachi's Z5010) for platinum ion, to confirm that the platinum ion/nitrogen atomic ratio was 120/62.

The particles contained in the particle-containing dendrimer 1b were observed by a transmission electron microscope (TEM), and the results indicated that the particles were uniform in size, having a diameter of 1.5 nm.

The reaction solution was spread on a washed PET base and dried to prepare the sample, which was analyzed for ESCA(Electron Spectroscopy for Chemical Analysis) to confirm that the chemical shift of Pt-$4f_{7/2}$ of the aqueous solution of $K_2[PtCl_4]$ was 71.3 eV, which corresponds to the chemical shift of metallic Pt. It was also confirmed that the chemical shift of N–1s of the dendrimer was 398.4 eV.

EXAMPLE 2

Preparation of Metallic Ion-dendrimer Complex

First, 10.0 mL of a 10 mM aqueous solution of $HAuCl_4$ ($10.0 \times 10^{-4}$ mol) was transferred to a 20 mL dropping funnel using a 50 mL Erlenmeyer flask. Next, 5.0 mL of a 0.5 mM aqueous solution of dendrimer [Starburst® (polyamine-based dendrimer (PAMAM), supplied by Aldrich, fourth generation, having 64 OH groups on the surface)] was transferred to another 50 mL Erlenmeyer flask, to which a gold ion solution was added dropwise at room temperature in 5 minutes with stirring by a magnetic stirrer, and the mixture was allowed to stand for 1 hour.

The reaction solution was dialyzed in a cellulose tube (supplied by VISKASE) for dialysis with 300 mL of deionized water twice a day.

The dialyzed gold ion-dendrimer complex was analyzed by elementary analysis (Perkin Elmer's 2400) for atomic nitrogen and atomic absorption spectrometer (Hitachi's Z5010) for gold ion, to confirm that the gold ion/nitrogen atomic ratio was 1/1.

Preparation of the Seed-containing Dendrimer 2a

The dialyzed gold ion-dendrimer complex was bubbled with a nitrogen gas for 3 hours, to which a given quantity of sodium borohydride was added little by little, while the nitrogen atmosphere was maintained, and the mixture was allowed to stand for 10 minutes, to prepare the seed-containing dendrimer 2a.

The resulting seed-containing dendrimer 2a was analyzed by elementary analysis (Perkin Elmer's 2400) for atomic nitrogen and atomic absorption spectrometer (Hitachi's Z5010) for gold ion, to confirm that the gold ion /nitrogen atomic ratio was 1/1. Size of the Au particles in the seed-containing dendrimer 2a was observed by a transmission electron microscope (TEM), and the results indicate that the particles were uniform in size, having a diameter of 1.3 nm.

Particle Growing Step

First, 6.2 mL of a 10 mM aqueous solution of $HAuCl_4$ ($6.2 \times 10^{-5}$ mol) was added dropwise to an aqueous solution containing the seed-containing dendrimer 2a at $1 \times 10^{-6}$ mol (as dendrimer) at room temperature in 5 minutes with stirring by a magnetic stirrer, and the mixture was allowed to stand for 1 minute. Then, a given quantity of sodium borohydride was added little by little in a nitrogen atmosphere, and the mixture was allowed to stand for 1 minute, to grow the particles.

The above step was repeated a total of 199 times, to grow the particles of the particle-containing dendrimer 2a into the particle-containing dendrimer 2b.

The particle-containing dendrimer 2b took a structure illustrated in FIG. 1. It was analyzed by elementary analysis (Perkin Elmer's 2400) for atomic nitrogen and atomic absorption spectrometer (Hitachi's Z5010) for gold ion, to confirm that the gold ion/nitrogen atomic ratio was in agreement with the level estimated from the added metal/dendrimer ratio. Size of the Au particles in the particle-containing dendrimer 2b was observed by a transmission electron microscope (TEM), and the results indicated that the particles were substantially uniform in size, having a diameter of 3.4 nm.

EXAMPLE 3

Preparation of Metallic Ion-dendrimer Complex

First, 10 mL of a 10 mM aqueous solution of $FeCl_3$ ($10.0 \times 10^{-4}$ mol) was transferred to a 20 mL dropping funnel using a 50 mL Erlenmeyer flask. Next, 5.0 mL of a 0.5 mM aqueous solution of dendrimer [Starburst® (polyamine-based dendrimer (PAMAM), supplied by Aldrich, fourth generation, having 64 OH groups on the surface)] was transferred to another 50 mL Erlenmeyer flask, to which an iron ion solution was added dropwise at room temperature in 5 minutes with stirring by a magnetic stirrer, and the mixture was allowed to stand for 1 hour.

The reaction solution was dialyzed in a cellulose tube (supplied by VISKASE) for dialysis with 300 mL of deionized water twice a day.

The dialyzed iron ion-dendrimer complex was analyzed by elementary analysis (Perkin Elmer's 2400) for atomic nitrogen and atomic absorption spectrometer (Hitachi's Z5010) for iron ion, to confirm that the iron ion/nitrogen atomic ratio was 1/1.

Preparation of the Seed-containing Dendrimer 3a

The dialyzed iron ion-dendrimer complex was bubbled with a nitrogen gas for 3 hours, to which a given quantity of sodium borohydride was added little by little, while the nitrogen atmosphere was maintained, and the mixture was allowed to stand for 10 minutes, to prepare the seed-containing dendrimer 3a.

The particle-containing dendrimer 3a was analyzed by elementary analysis (Perkin Elmer's 2400) for atomic nitrogen and atomic absorption spectrometer (Hitachi's Z5010) for iron ion, to confirm that the iron ion/nitrogen atomic ratio was 1/1. Size of the Fe particles in the particle-containing dendrimer 3a was observed by a transmission electron microscope (TEM), and the results indicated that the particles had a diameter of 1.1 nm.

Growth of the Particles

The step 1 described below was repeated a total of 99 times, and then the step 2 described below was repeated a total of 100 times, to grow the seed-containing dendrimer 3a into the particle-containing dendrimer 3b.

<Step 1>

First, 6.2mL of a 10 mM aqueous solution of $FeCl_3$ ($6.2 \times 10^{-5}$ mol) was added dropwise to an aqueous solution containing the particle-containing dendrimer at $1 \times 10^{-6}$ mol (as dendrimer) at room temperature in 5 minutes with stirring by a magnetic stirrer, and the mixture was allowed to stand for 1 minute. Then, a given quantity of sodium borohydride was added little by little in a nitrogen atmosphere, and the mixture was allowed to stand for 1 minute, to grow the particles.

<Step 2>

First, 6.2 mL of a 10 mM aqueous solution of $H_2[PtCl_4]$ ($6.2\times10^{-5}$ mol) was added dropwise to an aqueous solution containing the particle-containing dendrimer at $1\times10^{-6}$ mol (as dendrimer) at room temperature in 5 minutes with stirring by a magnetic stirrer, and the mixture was allowed to stand for 1 minute. Then, a given quantity of sodium borohydride was added little by little in a nitrogen atmosphere, and the mixture was allowed to stand for 1 minute, to grow the particles.

Analysis of the Particle-containing Dendrimer 3b

The particle-containing dendrimer 3b was analyzed by elementary analysis (Perkin Elmer's 2400) for atomic nitrogen and atomic absorption spectrometer (Hitachi's Z5010) for metallic atom, to confirm that the metallic atom/nitrogen atomic ratio was 1/1. Size of the metallic particles in the particle-containing dendrimer 3b was observed by a transmission electron microscope (TEM), and the results indicated that the particles were substantially uniform in size, having a diameter of 3.2 nm.

The particle-containing dendrimer 3b was spread on a silicon wafer using an XPS (Physical Electronics's PHI5300) and dried to prepare the sample. It was observed to have a peak corresponding to that of iron element (Fe-2p3/2, 707.0 eV) and another peak corresponding to that of platinum element (Pt-4f7/2, 71.3 eV).

The XPS angular resolution analysis detected Pt element at a photoelectron take-off angle of 15° (detection depth: around 1 nm) but little Fe element, but detected both elements at 60° (detection depth: around 3 nm).

Figure 2:
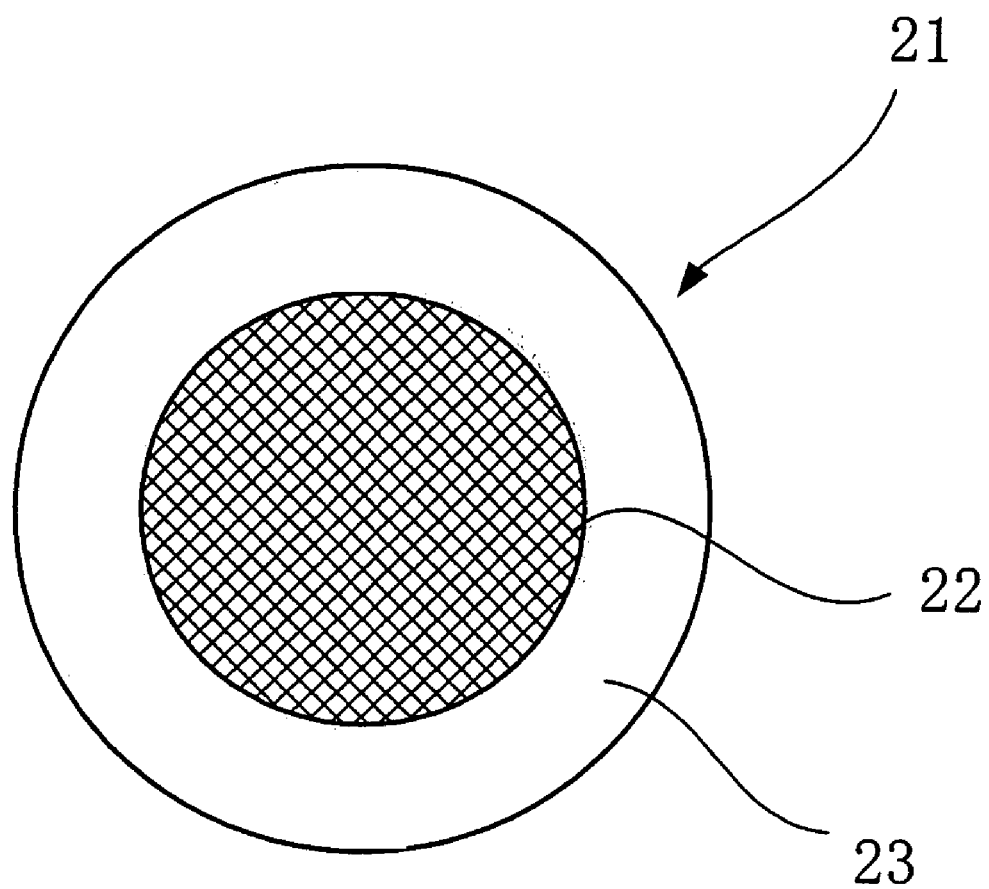
FIG. 2 illustrates a particle of three-dimensional, dendritic branching polymer and inorganic particle, prepared in EXAMPLE 3.

It was confirmed that the particle of core-shell structure with Pt on the surface and Fe inside, illustrated in FIG. 2, because of the observed dependence of Pt element concentration on photoelectron take-off angle.

EXAMPLE 4

Preparation of the Particle-containing Dendrimers 4a to 4b

First, 3.1 mL of each of the 5 mM aqueous metallic ion solutions given in Table 1 ($3.1\times10^{-5}$ mol) was added to an aqueous solution containing the particle-containing dendrimer 3b, prepared in EXAMPLE 3, at $1\times10^{-6}$ mol (as dendrimer) at room temperature in 5 minutes with stirring, and the mixture was allowed to stand for 1 minute. Then, a given quantity of sodium borohydride was added little by little to the above mixture, while the nitrogen atmosphere was maintained, and the resulting mixture was allowed to stand for 1 minute to grow the particles.

TABLE 1

| | Aqueous solution of metallic ion |
|---|---|
| Dendrimer 4a | $RuCl_3$ |
| Dendrimer 4b | $NiCl_2$ |
| Dendrimer 4c | $CoCl_2$ |
| Dendrimer 4d | $Na_2MoO_4(2H_2O)$ |

Analysis of the Particle-containing Dendrimers 4a to 4d

Each of the particle-containing dendrimers 4a to 4d was analyzed by elementary analysis (Perkin Elmer's 2400) for atomic nitrogen and atomic absorption spectrometer (Hitachi's Z5010) for metallic ion, to confirm that the metallic ion/nitrogen atomic ratio was in agreement with the level estimated from the added metal/dendrimer ratio.

Size of the metallic particles in each of the particle-containing dendrimers 4a to 4d was observed by a transmission electron microscope (TEM), and the results indicated that the particles were substantially uniform in size. The XPS analysis observed Ru, Ni, Co and Mo on part of the surface of the particle of core-shell structure with Fe inside and Pt on the surface.

EXAMPLE 5

Preparation of Dendron with Mercapto Group at the Focal Site

A mixture of 1.61 g (2.0 mmol) of 3,5-bis[3,5-bis(benzyloxy)benzyloxy]benzyl bromide, 0.18 g (2.4 mmol) of thiourea and 10 mL of dimethyl sulfoxide (DMSO) was stirred at room temperature for one night to prepare the reaction mixture. The resulting reaction mixture was incorporated with 5 mL of a 10% (by mass) aqueous solution of sodium hydroxide, and the mixture was stirred at room temperature for 1 hour. Then, the stirred mixture was adjusted at pH 2 to 3 with diluted hydrochloric acid, and extracted with ethyl acetate. The ethyl acetate layer was washed with saturated saline solution, dried by magnesium sulfate, and treated to removed the solvent, to prepare 1.38 g of the dendron, represented by the dendritic branching molecule (9) shown below as an oily product with mercapto group at the focal site in a yield of 92%. The dendron with mercapto group at the focal site was identified by $^1$H-NMR spectral analysis with deuterated chloroform as the solvent.

<Dendritic Branching Molecule (9)>

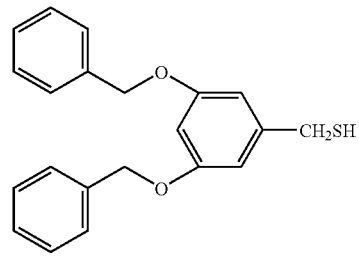

Preparation of Composite Nano-particles

A solution of 2.5 mg (7.4 mmol) of the dendron with mercapto group at the focal site, prepared above, dissolved in 5 mL of ethyl acetate was incorporated with a solution of 20.0 mg (58.8 mmol) of $HAuCl_4$ dissolved in 5 mL of ion-exchanged water, and stirred at room temperature for 1 hour to prepare the reaction solution. The reaction solution was incorporated with a solution of 6.7 mg (176.4 mmol) of sodium borohydride dissolved in methanol, and stirred at room temperature for 1 hour. The stirred reaction solution was treated by evaporation to solidify the ethyl acetate layer, to prepare 13.2 mg of the composite nano-particles with the dendron with mercapto group at the focal site, each arranged on the gold particle surface in a yield of 93%.

Figure 3:
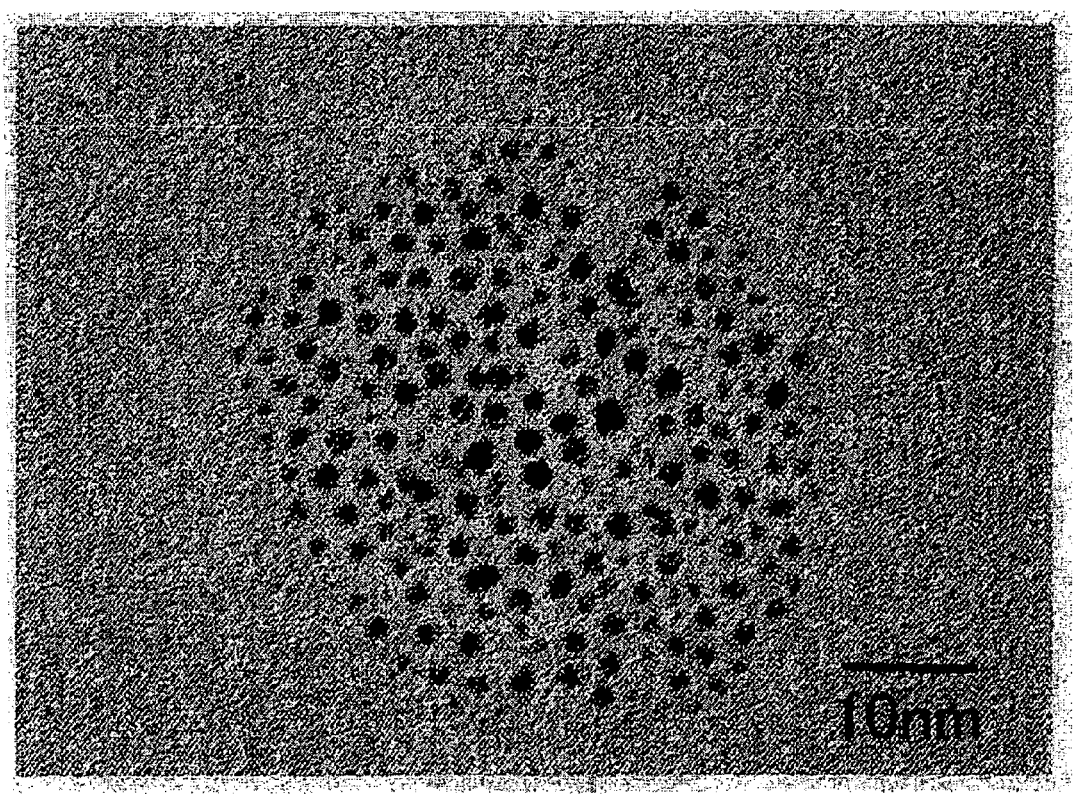
FIG. 3 is a TEM microgram of composite particle, with a gold particle coated with a dendron having a mercapto group on a focal site, prepared in EXAMPLE 5.

The composite nano-particle with the dendron with mercapto group at the focal site, arranged on the gold particle surface, was observed by a transmission electron microscope (TEM) (JOEL's JEM-2010). The TEM micrograph is given in FIG. 3.

The gold particles were almost uniform in size, having an average size of 1.75 nm, and narrow size distribution of 0.40 nm, determined by the digital caliper method (n=1000)

based on the TEM microgram, from which it was judged that the monodisperse, composite nano-particles were obtained. It was also found that they were configured by their self-collecting characteristics.

EXAMPLE 6

Preparation of Platinum Ion-dendrimer Complex

First, 10.0 mL of a 15 mM aqueous solution of $K_2[PtCl_4]$ ($15.0\times10^{-5}$ mol) was transferred to a 20 mL dropping funnel using a 50 mL Erlenmeyer flask. Next, 5.0 mL of a 0.5 mM aqueous solution of dendrimer [Starburst® (polyamine-based dendrimer (PAMAM), supplied by Aldrich, fourth generation, having 64 OH groups on the surface)] was transferred to another 50 mL Erlenmeyer flask, to which a platinum ion solution was added dropwise at room temperature in 5 minutes with stirring by a magnetic stirrer, and the mixture was stirred at 50° C. for 5 hours, to prepare the metallic ion-dendrimer complex solution.

Preparation of the Particle-containing Dendrimer

Figure 6:
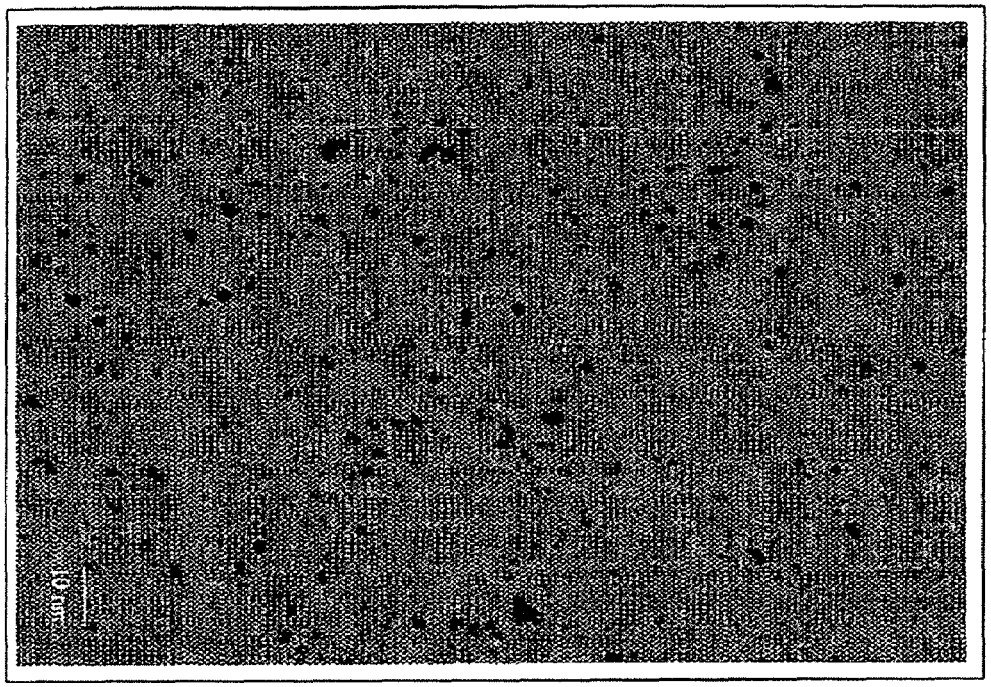
FIG. 6 is a TEM microgram of a nano-particle prepared in EXAMPLE 6 by incorporating a reducing solution at a stroke in a dendrimer solution in which a metal complex is formed.

The resulting platinum ion-dendrimer complex solution was incorporated with an aqueous solution of sodium borohydride ($NaBH_4$, $150.0\times10^{-5}$ mol) at a stroke, and the mixture was stirred under heating at 70° C. for 4 hours, to prepare the particle-containing dendrimer. FIG. 6 shows the transmission electron microscopic (TEM) microgram of the particle-containing dendrimer.

Figure 7:
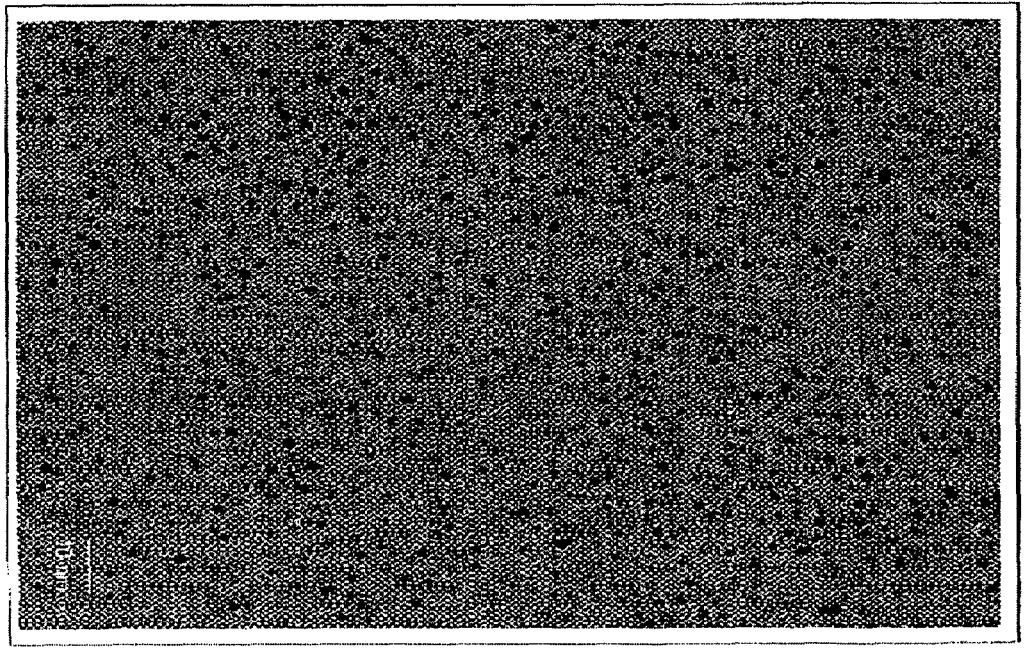
FIG. 7 is a TEM microgram of a nano-particle prepared in EXAMPLE 6 by simultaneously incorporating a dendrimer solution in which a metal complex is formed and reducing solution.

The platinum ion-dendrimer complex solution (0.05 mL) and aqueous sodium borohydride solution (0.05 mL) were simultaneously transferred dropwise at the same rate of 0.2 mL/minute in a beaker, through the syringe A and syringe B, as shown in FIG. 4. The mixture was stirred under heating at 70° C. for 4 hours, to prepare the particle-containing dendrimer. FIG. 7 shows the transmission electron microscopic (TEM) microgram of the particle-containing dendrimer.

Comparing the microgram shown in FIG. 6 with that shown in FIG. 7, it was found that mixing of the platinum ion-dendrimer complex solution and aqueous sodium borohydride solution by simultaneously dropping them gave the particles of narrower size distribution than mixing them at a stroke.

EXAMPLE 7

A solution of 2.5 mg (7.4 mmol) of the dendron prepared in the same manner as in EXAMPLE 5 dissolved in 5 mL of ethyl acetate was mixed with an aqueous solution of 20.0 mg (58.8 mmol) of $HAuCl_4$ dissolved in 5 mL of ion-exchanged water. The mixed solution (0.05 mL) and a solution (0.05 mL) prepared by dissolving 6.7 mg (176.4 mmol) of sodium borohydride in 5 mL of ion-exchanged water were simultaneously transferred dropwise at the same rate of 0.2 mL/minute in a beaker, through the syringe A and syringe B, as shown in FIG. 4. The resulting mixture was stirred at room temperature 1 hour.

The composite nano-particle with the dendron coated with gold was observed by a transmission electron microscope (TEM) (JOEL's JEM-2010). The composite nano-particles with the dendron coated with gold were observed to be almost uniform in size, having an average size of 1.67 nm, and narrow size distribution of 0.21 nm, from which it was judged that the monodisperse, composite nano-particles were obtained.

The results of EXAMPLE 7 also indicated that mixing of the gold ion-dendron complex solution and methanol solution of sodium borohydride by simultaneously dropping them gave the particles of narrower size distribution than mixing them at a stroke, as was done in EXAMPLE 5.

The nano-particles produced by the process of the present invention for producing nano-particles are the monodisperse particles uniform in size and substantially uniform in composition. As such, they are applicable to all areas which use nano-particles of metal, semiconducting crystal, metallic chalcogenide or metal halide, in particular to those areas which can have improved performance by use of monodisperse particles. These areas include, materials for high-density recording materials, catalysts, fuel cells, silver halide photoconductor materials, electrophotography, anti-dazzling films, and optical films, e.g., light-guiding plates.

What is claimed is:

1. A process for producing nano-particles, comprising the steps of:
    allowing dendritic branching molecules to capture particle precursors by adding a liquid containing the particle precursors to a liquid containing the dendritic branching molecules; and
    allowing the particle precursors captured by the dendritic branching molecules to transform and form into particles,
    wherein the transformation is carried out in a presence of a liquid containing a reducing agent; and
    the liquid containing the dendritic branching molecules capturing the particle precursors and the liquid containing a reducing agent are added simultaneously at the same addition rate.

2. A process for producing nano-particles according to claim 1, wherein each of the dendritic branching molecules is at least one selected from a fan-shaped dendritic branching molecule, a dendrimer, and a hyper-branch polymer.

3. A process for producing nano-particles according to claim 1, wherein the dendritic branching molecules are included in at least a portion of another material.

4. A process for producing nano-particles according to claim 1, wherein each of the dendritic branching molecules contains a benzene ring.

5. A process for producing nano-particles according to claim 1, wherein each of the dendritic branching molecules has a weight-average molecular weight of 200 or more.

6. A process for producing nano-particles according to claim 1, wherein each of the dendritic branching molecules has a generation number of at least 1.

7. A process for producing nano-particles according to claim 1, wherein each of the dendritic branching molecules has a focal site containing at least one of a functional group to which one of the particle precursors can bind, and a functional group to which the particle precursor can interact electrostatically.

8. A process for producing nano-particles according to claim 7, wherein the focal site contains a mercapto group.

9. A process for producing nano-particles according to claim 7, wherein each of the particle precursors is captured by one of the dendritic branching molecules at the focal site.

10. A process for producing nano-particles according to claim 9, wherein each of the particle precursors is more interactive with each of the dendritic branching molecules at the focal site than at a site thereof other than the focal site.

11. A process for producing nano-particles according to claim 1, wherein the transformation in the step of allowing the particle precursors to transform and form into particles is based on reduction.

12. A process for producing nano-particles according to claim 1, wherein the liquid containing the dendritic branching molecules capturing the particle precursors and the liquid containing a reducing agent are mixed while being heated.

13. A process for producing nano-particles according to claim 1, further comprising the step of allowing the particles to grow after the step of allowing the particle precursors to transform and form into particles.

14. A process for producing nano-particles according to claim 13, wherein the step of allowing the particles to grow is carried out by adding a liquid containing particle precursors, allowing the dendritic branching molecules to capture the particle precursors, and allowing the particle precursors to transform and form into particles.

15. A process for producing nano-particles according to claim 13, wherein the step of allowing the particles to grow is carried out at least once.

16. A process for producing nano-particles according to claim 13, wherein each of the dendritic branching molecules has a focal site, and wherein the number of the particle precursors added is equal to or less than the number of the focal sites of the dendritic branching molecules in the step of allowing the particles to grow.

17. A process for producing nano-particles according to claim 14, wherein the particle precursors added in the step of allowing the particles to grow is one of the same as and different from the particle precursors added in the step of allowing dendritic branching molecules to capture particle precursors.

18. A process for producing nano-particles according to claim 1, wherein each of the particle precursors is a metallic ion.

19. A process for producing nano-particles according to claim 18, wherein the metallic ion is at least one selected from Group 3A, 4A, 5A, 6A, 7A, 8, 1B, 2B, 3B, and 6B elements in the periodic table.

20. A process for producing nano-particles according to claim 1, wherein each of the particles is at least one of an inorganic particle and an organic particle.

21. A process for producing nano-particles according to claim 20, wherein the inorganic particle is metallic.

* * * * *